United States Patent
Uemori et al.

(10) Patent No.: US 6,395,526 B1
(45) Date of Patent: May 28, 2002

(54) DNA POLYMERASE

(75) Inventors: Takashi Uemori, Otsu; Yoshizumi Ishino, Takatsuki; Ikunoshin Kato, Uji, all of (JP)

(73) Assignee: Takara Shuzo Co., Ltd., Kyoto (JP)

( * ) Notice: Subject to any disclaimer, the term of this patent is extended or adjusted under 35 U.S.C. 154(b) by 0 days.

(21) Appl. No.: 09/091,889

(22) PCT Filed: Dec. 26, 1996

(86) PCT No.: PCT/JP96/03869

§ 371 (c)(1),
(2), (4) Date: Jun. 26, 1998

(87) PCT Pub. No.: WO97/24444

PCT Pub. Date: Jul. 10, 1997

(30) Foreign Application Priority Data

Dec. 27, 1995 (JP) ............................... 7-353778

(51) Int. Cl.⁷ ............................. C12N 9/12; C07H 21/04
(52) U.S. Cl. ............... 435/194; 435/252.3; 435/254.11; 435/325; 435/320.1; 435/410; 536/23.1; 536/23.2
(58) Field of Search ............................. 435/194, 252.3, 435/254.11, 325, 410, 320.1; 536/23.2, 23.1

(56) References Cited

U.S. PATENT DOCUMENTS 5,352,778 A    10/1994   Comb et al. ............... 536/23.2
5,489,523 A    2/1996    Mathur ...................... 435/194
5,545,552 A    8/1996    Mathur ..................... 435/252.3

FOREIGN PATENT DOCUMENTS

| EP | 0455430 A2 | 11/1991 |
| EP | 0547359 A1 | 6/1993 |
| EP | 0624641 A2 | 11/1994 |
| EP | 0669401 A2 * | 8/1995 |

OTHER PUBLICATIONS

Smith et al., J. Biochem., vol. 277 (1991) pp. 255–261.

* cited by examiner

Primary Examiner—Rebecca E. Prouty
Assistant Examiner—Richard G Hutson
(74) Attorney, Agent, or Firm—Birch, Stewart, Kolasch & Birch, LLP

(57) ABSTRACT

The present invention relates to a DNA polymerase possesses the properties of 1) exhibiting higher polymerase activity when assayed by using as a substrate a complex resulting from primer annealing to a single stranded template DNA, as compared to the case where an activated DNA is used as a substrate; 2) possessing a 3'→5' exonuclease activity; 3) being capable of amplifying a DNA fragment of about 20 kbp, in the case where polymerase chain reaction (PCR) is carried out using λ-DNA as a template. It also relates to a DNA polymerase-constituting protein; a DNA containing the base sequence encoding thereof; and a method for producing the DNA polymerase. The present invention provides a novel DNA polymerase possessing both a high primer extensibility and a 3'→5' exonuclease activity.

12 Claims, 6 Drawing Sheets

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 1839 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (ix) FEATURE:
      (A) NAME/KEY: CDS
      (B) LOCATION: 1..1839

(xi) SEQUENCE DESCRIPTION: SEQ ID NO:1:

```
ATG GAT GAA TTT GTA AAA TCA CTT CTA AAA G CT AAC TAT CTA ATA ACT       48
Met Asp Glu Phe Val Lys Ser Leu Leu Lys A la Asn Tyr Leu Ile Thr
 1               5                  10                  15
```

```
CCC TCT GCC TAC TAT CTC TTG AGA GAA TAC T AT GAA AAA GGT GAA TTC          96
Pro Ser Ala Tyr Tyr Leu Leu Arg Glu Tyr T yr Glu Lys Gly Glu Phe
            20                  25                  30

TCA ATT GTG GAG CTG GTA AAA TTT GCA AGA T CA AGA GAG AGC TAC ATA         144
Ser Ile Val Glu Leu Val Lys Phe Ala Arg S er Arg Glu Ser Tyr Ile
                35                  40                  45

ATT ACT GAT GCT TTA GCA ACA GAA TTC CTT A AA GTT AAA GGC CTT GAA         192
Ile Thr Asp Ala Leu Ala Thr Glu Phe Leu L ys Val Lys Gly Leu Glu
        50                  55                  60

CCA ATT CTT CCA GTG GAA ACA AAG GGG GGT T TT GTT TCC ACT GGA GAG         240
Pro Ile Leu Pro Val Glu Thr Lys Gly Gly P he Val Ser Thr Gly Glu
65                  70                  75                  80

TCC CAA AAA GAG CAG TCT TAT GAA GAG TCT T TT GGG ACT AAA GAA GAA         288
Ser Gln Lys Glu Gln Ser Tyr Glu Glu Ser P he Gly Thr Lys Glu Glu
                85                  90                  95

ATT TCC CAG GAG ATT AAA GAA GGA GAG AGT T TT ATT TCC ACT GGA AGT         336
Ile Ser Gln Glu Ile Lys Glu Gly Glu Ser P he Ile Ser Thr Gly Ser
            100                 105                 110

GAA CCA CTT GAA GAG GAG CTC AAT AGC ATT G GA ATT GAG GAA ATT GGG         384
Glu Pro Leu Glu Glu Glu Leu Asn Ser Ile G ly Ile Glu Glu Ile Gly
        115                 120                 125

GCA AAT GAA GAG TTA GTT TCT AAT GGA AAT G AC AAT GGT GGA GAG GCA         432
Ala Asn Glu Glu Leu Val Ser Asn Gly Asn A sp Asn Gly Gly Glu Ala
130                 135                 140

ATT GTC TTT GAC AAA TAT GGC TAT CCA ATG G TA TAT GCT CCA GAA GAA         480
Ile Val Phe Asp Lys Tyr Gly Tyr Pro Met V al Tyr Ala Pro Glu Glu
145                 150                 155                 160

ATA GAG GTT GAG GAG AAG GAG TAC TCG AAG T AT GAA GAT CTG ACA ATA         528
Ile Glu Val Glu Glu Lys Glu Tyr Ser Lys T yr Glu Asp Leu Thr Ile
                165                 170                 175

CCC ATG AAC CCC GAC TTC AAT TAT GTG GAA A TA AAG GAA GAT TAT GAT         576
Pro Met Asn Pro Asp Phe Asn Tyr Val Glu I le Lys Glu Asp Tyr Asp
            180                 185                 190

GTT GTC TTC GAT GTT AGG AAT GTA AAG CTG A AG CCT CCT AAG GTA AAG         624
Val Val Phe Asp Val Arg Asn Val Lys Leu L ys Pro Pro Lys Val Lys
        195                 200                 205

AAC GGT AAT GGG AAG GAA GGT GAA ATA ATT G TT GAA GCT TAT GCT TCT         672
Asn Gly Asn Gly Lys Glu Gly Glu Ile Ile V al Glu Ala Tyr Ala Ser
210                 215                 220

CTC TTC AGG AGT AGG TTG AAG AAG TTA AGG A AA ATA CTA AGG GAA AAT         720
Leu Phe Arg Ser Arg Leu Lys Lys Leu Arg L ys Ile Leu Arg Glu Asn
225                 230                 235                 240

CCT GAA TTG GAC AAT GTT GTT GAT ATT GGG A AG CTG AAG TAT GTG AAG         768
Pro Glu Leu Asp Asn Val Val Asp Ile Gly L ys Leu Lys Tyr Val Lys
                245                 250                 255

GAA GAT GAA ACC GTG ACA ATA ATA GGG CTT G TC AAT TCC AAG AGG GAA         816
Glu Asp Glu Thr Val Thr Ile Ile Gly Leu V al Asn Ser Lys Arg Glu
            260                 265                 270

GTG AAT AAA GGA TTG ATA TTT GAA ATA GAA G AT CTC ACA GGA AAG GTT         864
Val Asn Lys Gly Leu Ile Phe Glu Ile Glu A sp Leu Thr Gly Lys Val
        275                 280                 285

AAA GTT TTC TTG CCG AAA GAT TCG GAA GAT T AT AGG GAG GCA TTT AAG         912
Lys Val Phe Leu Pro Lys Asp Ser Glu Asp T yr Arg Glu Ala Phe Lys
290                 295                 300

GTT CTT CCA GAT GCC GTC GTC GCT TTT AAG G GG GTG TAT TCA AAG AGG         960
Val Leu Pro Asp Ala Val Val Ala Phe Lys G ly Val Tyr Ser Lys Arg
305                 310                 315                 320

GGA ATT TTG TAC GCC AAC AAG TTT TAC CTT C CA GAC GTT CCC CTC TAT        1008
Gly Ile Leu Tyr Ala Asn Lys Phe Tyr Leu P ro Asp Val Pro Leu Tyr
```

|  |  |  |  |  |  |  |  |  |
|---|---|---|---|---|---|---|---|---|
|  |  | 325 |  | 330 |  |  | 335 |  |
| AGG | AGA | CAA | AAG | CCT | CCA | CTG GAA | GAG AAA G TT TAT GCT ATT CTC ATA | 1056 |
| Arg | Arg | Gln | Lys | Pro | Pro | Leu Glu | Glu Lys V al Tyr Ala Ile Leu Ile |  |
|  |  |  | 340 |  |  | 345 | 350 |  |
| AGT GAT ATA CAC GTC GGA AGT AAA GAG TTC T GC GAA AAT GCC TTC ATA | 1104 |
| Ser Asp Ile His Val Gly Ser Lys Glu Phe C ys Glu Asn Ala Phe Ile |  |
| 355 360 365 |  |
| AAG TTC TTA GAG TGG CTC AAT GGA AAC GTT G AA ACT AAG GAA GAG GAA | 1152 |
| Lys Phe Leu Glu Trp Leu Asn Gly Asn Val G lu Thr Lys Glu Glu Glu |  |
| 370 375 380 |  |
| GAA ATC GTG AGT AGG GTT AAG TAT CTA ATC A TT GCA GGA GAT GTT GTT | 1200 |
| Glu Ile Val Ser Arg Val Lys Tyr Leu Ile I le Ala Gly Asp Val Val |  |
| 385 390 395 400 |  |
| GAT GGT GTT GGC GTT TAT CCG GGC CAG TAT G CC GAC TTG ACG ATT CCA | 1248 |
| Asp Gly Val Gly Val Tyr Pro Gly Gln Tyr A la Asp Leu Thr Ile Pro |  |
| 405 410 415 |  |
| GAT ATA TTC GAC CAG TAT GAG GCC CTC GCA A AC CTT CTC TCT CAC GTT | 1296 |
| Asp Ile Phe Asp Gln Tyr Glu Ala Leu Ala A sn Leu Leu Ser His Val |  |
| 420 425 430 |  |
| CCT AAG CAC ATA ACA ATG TTC ATT GCC CCA G GA AAC CAC GAT GCT GCT | 1344 |
| Pro Lys His Ile Thr Met Phe Ile Ala Pro G ly Asn His Asp Ala Ala |  |
| 435 440 445 |  |
| AGG CAA GCT ATT CCC CAA CCA GAA TTC TAC A AA GAG TAT GCA AAA CCT | 1392 |
| Arg Gln Ala Ile Pro Gln Pro Glu Phe Tyr L ys Glu Tyr Ala Lys Pro |  |
| 450 455 460 |  |
| ATA TAC AAG CTC AAG AAC GCC GTG ATA ATA A GC AAT CCT GCT GTA ATA | 1440 |
| Ile Tyr Lys Leu Lys Asn Ala Val Ile Ile S er Asn Pro Ala Val Ile |  |
| 465 470 475 480 |  |
| AGA CTA CAT GGT AGG GAC TTT CTG ATA GCT C AT GGT AGG GGG ATA GAG | 1488 |
| Arg Leu His Gly Arg Asp Phe Leu Ile Ala H is Gly Arg Gly Ile Glu |  |
| 485 490 495 |  |
| GAT GTC GTT GGA AGT GTT CCT GGG TTG ACC C AT CAC AAG CCC GGC CTC | 1536 |
| Asp Val Val Gly Ser Val Pro Gly Leu Thr H is His Lys Pro Gly Leu |  |
| 500 505 510 |  |
| CCA ATG GTT GAA CTA TTG AAG ATG AGG CAT G TA GCT CCA ATG TTT GGA | 1584 |
| Pro Met Val Glu Leu Leu Lys Met Arg His V al Ala Pro Met Phe Gly |  |
| 515 520 525 |  |
| GGA AAG GTT CCA ATA GCT CCT GAT CCA GAA G AT TTG CTT GTT ATA GAA | 1632 |
| Gly Lys Val Pro Ile Ala Pro Asp Pro Glu A sp Leu Leu Val Ile Glu |  |
| 530 535 540 |  |
| GAA GTT CCT GAT GTA GTT CAC ATG GGT CAC G TT CAC GTT TAC GAT GCG | 1680 |
| Glu Val Pro Asp Val Val His Met Gly His V al His Val Tyr Asp Ala |  |
| 545 550 555 560 |  |
| GTA GTT TAT AGG GGA GTT CAG CTG GTT AAC T CC GCC ACC TGG CAG GCT | 1728 |
| Val Val Tyr Arg Gly Val Gln Leu Val Asn S er Ala Thr Trp Gln Ala |  |
| 565 570 575 |  |
| CAG ACC GAG TTC CAG AAG ATG GTG AAC ATA G TT CCA ACG CCT GCA AAG | 1776 |
| Gln Thr Glu Phe Gln Lys Met Val Asn Ile V al Pro Thr Pro Ala Lys |  |
| 580 585 590 |  |
| GTT CCC GTT GTT GAT ATT GAT ACT GCA AAA G TT GTC AAG GTT TTG GAC | 1824 |
| Val Pro Val Val Asp Ile Asp Thr Ala Lys V al Val Lys Val Leu Asp |  |
| 595 600 605 |  |
| TTT AGT GGG TGG TGC | 1839 |
| Phe Ser Gly Trp Cys |  |
| 610 |  |

(2) INFORMATION FOR SEQ ID NO:2:

(i) SEQUENCE CHARACTERISTICS:
       (A) LENGTH: 613 amino acids (B) TYPE: amino acid
        (D) TOPOLOGY: linear (ii) MOLECULE TYPE: peptide (xi) SEQUENCE DESCRIPTION: SEQ ID NO:2:

```
Met Asp Glu Phe Val Lys Ser Leu Leu Lys Ala Asn Tyr Leu Ile Thr
 1               5                  10                  15

Pro Ser Ala Tyr Tyr Leu Leu Arg Glu Tyr Tyr Glu Lys Gly Glu Phe
                20                  25                  30

Ser Ile Val Glu Leu Val Lys Phe Ala Arg Ser Arg Glu Ser Tyr Ile
                35                  40                  45

Ile Thr Asp Ala Leu Ala Thr Glu Phe Leu Lys Val Lys Gly Leu Glu
        50                  55                  60

Pro Ile Leu Pro Val Glu Thr Lys Gly Gly Phe Val Ser Thr Gly Glu
 65                  70                  75                  80

Ser Gln Lys Glu Gln Ser Tyr Glu Glu Ser Phe Gly Thr Lys Glu Glu
                85                  90                  95

Ile Ser Gln Glu Ile Lys Glu Gly Glu Ser Phe Ile Ser Thr Gly Ser
               100                 105                 110

Glu Pro Leu Glu Glu Glu Leu Asn Ser Ile Gly Ile Glu Glu Ile Gly
               115                 120                 125

Ala Asn Glu Glu Leu Val Ser Asn Gly Asn Asp Asn Gly Gly Glu Ala
       130                 135                 140

Ile Val Phe Asp Lys Tyr Gly Tyr Pro Met Val Tyr Ala Pro Glu Glu
145                 150                 155                 160

Ile Glu Val Glu Glu Lys Glu Tyr Ser Lys Tyr Glu Asp Leu Thr Ile
               165                 170                 175

Pro Met Asn Pro Asp Phe Asn Tyr Val Glu Ile Lys Glu Asp Tyr Asp
               180                 185                 190

Val Val Phe Asp Val Arg Asn Val Lys Leu Lys Pro Pro Lys Val Lys
       195                 200                 205

Asn Gly Asn Gly Lys Glu Gly Glu Ile Ile Val Glu Ala Tyr Ala Ser
       210                 215                 220

Leu Phe Arg Ser Arg Leu Lys Lys Leu Arg Lys Ile Leu Arg Glu Asn
225                 230                 235                 240

Pro Glu Leu Asp Asn Val Val Asp Ile Gly Lys Leu Lys Tyr Val Lys
               245                 250                 255

Glu Asp Glu Thr Val Thr Ile Ile Gly Leu Val Asn Ser Lys Arg Glu
               260                 265                 270

Val Asn Lys Gly Leu Ile Phe Glu Ile Glu Asp Leu Thr Gly Lys Val
       275                 280                 285

Lys Val Phe Leu Pro Lys Asp Ser Glu Asp Tyr Arg Glu Ala Phe Lys
       290                 295                 300

Val Leu Pro Asp Ala Val Val Ala Phe Lys Gly Val Tyr Ser Lys Arg
305                 310                 315                 320

Gly Ile Leu Tyr Ala Asn Lys Phe Tyr Leu Pro Asp Val Pro Leu Tyr
               325                 330                 335

Arg Arg Gln Lys Pro Pro Leu Glu Glu Lys Val Tyr Ala Ile Leu Ile
       340                 345                 350

Ser Asp Ile His Val Gly Ser Lys Glu Phe Cys Glu Asn Ala Phe Ile
       355                 360                 365

Lys Phe Leu Glu Trp Leu Asn Gly Asn Val Glu Thr Lys Glu Glu Glu
370                 375                 380
```

```
Glu Ile Val Ser Arg Val Lys Tyr Leu Ile Ile Ala Gly Asp Val Val
385                 390                 395                 400

Asp Gly Val Gly Val Tyr Pro Gly Gln Tyr Ala Asp Leu Thr Ile Pro
                405                 410                 415

Asp Ile Phe Asp Gln Tyr Glu Ala Leu Ala Asn Leu Leu Ser His Val
            420                 425                 430

Pro Lys His Ile Thr Met Phe Ile Ala Pro Gly Asn His Asp Ala Ala
        435                 440                 445

Arg Gln Ala Ile Pro Gln Pro Glu Phe Tyr Lys Glu Tyr Ala Lys Pro
450                 455                 460

Ile Tyr Lys Leu Lys Asn Ala Val Ile Ile Ser Asn Pro Ala Val Ile
465                 470                 475                 480

Arg Leu His Gly Arg Asp Phe Leu Ile Ala His Gly Arg Gly Ile Glu
                485                 490                 495

Asp Val Val Gly Ser Val Pro Gly Leu Thr His His Lys Pro Gly Leu
                500                 505                 510

Pro Met Val Glu Leu Leu Lys Met Arg His Val Ala Pro Met Phe Gly
            515                 520                 525

Gly Lys Val Pro Ile Ala Pro Asp Pro Glu Asp Leu Leu Val Ile Glu
530                 535                 540

Glu Val Pro Asp Val Val His Met Gly His Val His Val Tyr Asp Ala
545                 550                 555                 560

Val Val Tyr Arg Gly Val Gln Leu Val Asn Ser Ala Thr Trp Gln Ala
                565                 570                 575

Gln Thr Glu Phe Gln Lys Met Val Asn Ile Val Pro Thr Pro Ala Lys
            580                 585                 590

Val Pro Val Val Asp Ile Asp Thr Ala Lys Val Val Lys Val Leu Asp
                595                 600                 605

Phe Ser Gly Trp Cys
        610

(2) INFORMATION FOR SEQ ID NO:3:

(i) SEQUENCE CHARACTERISTICS:
        (A) LENGTH: 3789 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (ix) FEATURE:
        (A) NAME/KEY: CDS
        (B) LOCATION: 1..3789

(xi) SEQUENCE DESCRIPTION: SEQ ID NO:3:

ATG GAG CTT CCA AAG GAA ATT GAG GAG TAT TTT GAG ATG CTT CAA AGG    48
Met Glu Leu Pro Lys Glu Ile Glu Glu Tyr Phe Glu Met Leu Gln Arg
  1               5                  10                  15

GAA ATT GAC AAA GCT TAC GAG ATT GCT AAG AAG GCT AGG AGT CAG GGT    96
Glu Ile Asp Lys Ala Tyr Glu Ile Ala Lys Lys Ala Arg Ser Gln Gly
             20                  25                  30

AAA GAC CCC TCA ACC GAT GTT GAG ATT CCC CAG GCT ACA GAC ATG GCT   144
Lys Asp Pro Ser Thr Asp Val Glu Ile Pro Gln Ala Thr Asp Met Ala
         35                  40                  45

GGA AGA GTT GAG AGC TTA GTT GGC CCT CCC GGA GTT GCT CAG AGA ATT   192
Gly Arg Val Glu Ser Leu Val Gly Pro Pro Gly Val Ala Gln Arg Ile
 50                  55                  60
```

| | | |
|---|---|---|
| AGG GAG CTT TTA AAA GAG TAT GAT AAG GAA A TT GTT GCT TTA AAG ATA<br>Arg Glu Leu Leu Lys Glu Tyr Asp Lys Glu I le Val Ala Leu Lys Ile<br>65                                 70                            75                           80 | 240 |
| GTT GAT GAG ATA ATT GAG GGC AAA TTT GGT G AT TTT GGA AGT AAA GAG<br>Val Asp Glu Ile Ile Glu Gly Lys Phe Gly A sp Phe Gly Ser Lys Glu<br>                               85                                90                            95 | 288 |
| AAG TAC GCT GAA CAG GCT GTA AGG ACA GCC T TG GCA ATA TTA ACT GAG<br>Lys Tyr Ala Glu Gln Ala Val Arg Thr Ala L eu Ala Ile Leu Thr Glu<br>                         100                           105                           110 | 336 |
| GGT ATT GTT TCT GCT CCA CTT GAG GGT ATA G CT GAT GTT AAA ATC AAG<br>Gly Ile Val Ser Ala Pro Leu Glu Gly Ile A la Asp Val Lys Ile Lys<br>                     115                           120                           125 | 384 |
| CGA AAC ACC TGG GCT GAT AAC TCT GAA TAC C TC GCC CTT TAC TAT GCT<br>Arg Asn Thr Trp Ala Asp Asn Ser Glu Tyr L eu Ala Leu Tyr Tyr Ala<br>130                           135                            140 | 432 |
| GGG CCA ATT AGG AGT TCT GGT GGA ACT GCT C AA GCT CTC AGT GTA CTT<br>Gly Pro Ile Arg Ser Ser Gly Gly Thr Ala G ln Ala Leu Ser Val Leu<br>145                           150                           155                           160 | 480 |
| GTT GGT GAT TAC GTT AGG CGA AAG CTT GGC C TT GAT AGG TTT AAG CCA<br>Val Gly Asp Tyr Val Arg Arg Lys Leu Gly L eu Asp Arg Phe Lys Pro<br>                     165                           170                           175 | 528 |
| AGT GGG AAG CAT ATA GAG AGA ATG GTT GAG G AA GTT GAC CTC TAT CAT<br>Ser Gly Lys His Ile Glu Arg Met Val Glu G lu Val Asp Leu Tyr His<br>                     180                           185                           190 | 576 |
| AGA GCT GTT TCA AGG CTT CAA TAT CAT CCC T CA CCT GAT GAA GTG AGA<br>Arg Ala Val Ser Arg Leu Gln Tyr His Pro S er Pro Asp Glu Val Arg<br>                     195                           200                           205 | 624 |
| TTA GCA ATG AGG AAT ATT CCC ATA GAA ATC A CT GGT GAA GCC ACT GAC<br>Leu Ala Met Arg Asn Ile Pro Ile Glu Ile T hr Gly Glu Ala Thr Asp<br>210                           215                            220 | 672 |
| GAT GTG GAG GTT TCC CAT AGA GAT GTA GAG G GA GTT GAG ACA AAT CAG<br>Asp Val Glu Val Ser His Arg Asp Val Glu G ly Val Glu Thr Asn Gln<br>225                           230                           235                           240 | 720 |
| CTG AGA GGA GGA GCG ATC CTA GTT TTG GCG G AG GGT GTT CTC CAG AAG<br>Leu Arg Gly Gly Ala Ile Leu Val Leu Ala G lu Gly Val Leu Gln Lys<br>                     245                           250                           255 | 768 |
| GCT AAA AAG CTC GTG AAA TAC ATT GAC AAG A TG GGG ATT GAT GGA TGG<br>Ala Lys Lys Leu Val Lys Tyr Ile Asp Lys M et Gly Ile Asp Gly Trp<br>                     260                           265                           270 | 816 |
| GAG TGG CTT AAA GAG TTT GTA GAG GCT AAA G AA AAA GGT GAA GAA ATC<br>Glu Trp Leu Lys Glu Phe Val Glu Ala Lys G lu Lys Gly Glu Glu Ile<br>                     275                           280                           285 | 864 |
| GAA GAG AGT GAA AGT AAA GCC GAG GAG TCA A AA GTT GAA ACA AGG GTG<br>Glu Glu Ser Glu Ser Lys Ala Glu Glu Ser L ys Val Glu Thr Arg Val<br>                     290                           295                           300 | 912 |
| GAG GTA GAG AAG GGA TTC TAC TAC AAG CTC T AT GAG AAA TTT AGG GCT<br>Glu Val Glu Lys Gly Phe Tyr Tyr Lys Leu T yr Glu Lys Phe Arg Ala<br>305                           310                           315                           320 | 960 |
| GAG ATT GCC CCA AGC GAA AAG TAT GCA AAG G AA ATA ATT GGT GGG AGG<br>Glu Ile Ala Pro Ser Glu Lys Tyr Ala Lys G lu Ile Ile Gly Gly Arg<br>                     325                           330                           335 | 1008 |
| CCG TTA TTC GCT GGA CCC TCG GAA AAT GGG G GA TTT AGG CTT AGA TAT<br>Pro Leu Phe Ala Gly Pro Ser Glu Asn Gly G ly Phe Arg Leu Arg Tyr<br>                     340                           345                           350 | 1056 |
| GGT AGA AGT AGG GTG AGT GGA TTT GCA ACA T GG AGC ATA AAT CCA GCA<br>Gly Arg Ser Arg Val Ser Gly Phe Ala Thr T rp Ser Ile Asn Pro Ala<br>                     355                           360                           365 | 1104 |
| ACA ATG GTT TTG GTT GAC GAG TTC TTG GCC A TT GGA ACT CAA ATG AAA<br>Thr Met Val Leu Val Asp Glu Phe Leu Ala I le Gly Thr Gln Met Lys | 1152 |

```
         370                375                380
ACC GAG AGG CCT GGG AAA GGT GCA GTA GTG A CT CCA GCA ACA ACC GCT      1200
Thr Glu Arg Pro Gly Lys Gly Ala Val Val T hr Pro Ala Thr Thr Ala
385                 390                395                400

GAA GGG CCG ATT GTT AAG CTA AAG GAT GGG A GT GTT GTT AGG GTT GAT      1248
Glu Gly Pro Ile Val Lys Leu Lys Asp Gly S er Val Val Arg Val Asp
                405                410                415

GAT TAC AAC TTG GCC CTC AAA ATA AGG GAT G AA GTC GAA GAG ATA CTT      1296
Asp Tyr Asn Leu Ala Leu Lys Ile Arg Asp G lu Val Glu Glu Ile Leu
                420                425                430

TAT TTG GGA GAT GCA ATC ATA GCC TTT GGA G AC TTT GTG GAG AAC AAT      1344
Tyr Leu Gly Asp Ala Ile Ile Ala Phe Gly A sp Phe Val Glu Asn Asn
                435                440                445

CAA ACT CTC CTT CCT GCA AAC TAT GTA GAG G AG TGG TGG ATC CAA GAG      1392
Gln Thr Leu Leu Pro Ala Asn Tyr Val Glu G lu Trp Trp Ile Gln Glu
                450                455                460

TTC GTA AAG GCC GTT AAT GAG GCA TAT GAA G TT GAG CTT AGA CCC TTT      1440
Phe Val Lys Ala Val Asn Glu Ala Tyr Glu V al Glu Leu Arg Pro Phe
465                 470                475                480

GAG GAA AAT CCC AGG GAG AGC GTT GAG GAA G CA GCA GAG TAC CTT GAA      1488
Glu Glu Asn Pro Arg Glu Ser Val Glu Glu A la Ala Glu Tyr Leu Glu
                485                490                495

GTT GAC CCA GAA TTC TTG GCT AAG ATG CTT T AC GAT CCT CTA AGG GTT      1536
Val Asp Pro Glu Phe Leu Ala Lys Met Leu T yr Asp Pro Leu Arg Val
                500                505                510

AAG CCT CCC GTG GAG CTA GCC ATA CAC TTC T CG GAA ATC CTG GAA ATT      1584
Lys Pro Pro Val Glu Leu Ala Ile His Phe S er Glu Ile Leu Glu Ile
                515                520                525

CCT CTC CAC CCA TAC TAC ACC CTT TAT TGG A AT ACT GTA AAT CCT AAA      1632
Pro Leu His Pro Tyr Tyr Thr Leu Tyr Trp A sn Thr Val Asn Pro Lys
530                 535                540

GAT GTT GAA AGA CTT TGG GGA GTA TTA AAA G AC AAG GCC ACC ATA GAA      1680
Asp Val Glu Arg Leu Trp Gly Val Leu Lys A sp Lys Ala Thr Ile Glu
545                 550                555                560

TGG GGC ACT TTC AGA GGT ATA AAG TTT GCA A AG AAA ATT GAA ATT AGC      1728
Trp Gly Thr Phe Arg Gly Ile Lys Phe Ala L ys Lys Ile Glu Ile Ser
                565                570                575

CTG GAC GAC CTG GGA AGT CTT AAG AGA ACC C TA GAG CTC CTG GGA CTT      1776
Leu Asp Asp Leu Gly Ser Leu Lys Arg Thr L eu Glu Leu Leu Gly Leu
                580                585                590

CCT CAT ACG GTA AGA GAA GGG ATT GTA GTG G TT GAT TAT CCG TGG AGT      1824
Pro His Thr Val Arg Glu Gly Ile Val Val V al Asp Tyr Pro Trp Ser
                595                600                605

GCA GCT CTT CTC ACT CCA TTG GGC AAT CTT G AA TGG GAG TTT AAG GCC      1872
Ala Ala Leu Leu Thr Pro Leu Gly Asn Leu G lu Trp Glu Phe Lys Ala
                610                615                620

AAG CCC TTC TAC ACT GTA ATA GAC ATC ATT A AC GAG AAC AAT CAG ATA      1920
Lys Pro Phe Tyr Thr Val Ile Asp Ile Ile A sn Glu Asn Asn Gln Ile
625                 630                635                640

AAG CTC AGG GAC AGG GGA ATA AGC TGG ATA G GG GCA AGA ATG GGA AGG      1968
Lys Leu Arg Asp Arg Gly Ile Ser Trp Ile G ly Ala Arg Met Gly Arg
                645                650                655

CCA GAG AAG GCA AAA GAA AGA AAA ATG AAG C CA CCT GTT CAA GTC CTC      2016
Pro Glu Lys Ala Lys Glu Arg Lys Met Lys P ro Pro Val Gln Val Leu
                660                665                670

TTC CCA ATT GGC TTG GCA GGG GGT TCT AGC A GA GAT ATA AAG AAG GCT      2064
Phe Pro Ile Gly Leu Ala Gly Gly Ser Ser A rg Asp Ile Lys Lys Ala
                675                680                685

GCT GAA GAG GGA AAA ATA GCT GAA GTT GAG A TT GCT TTC TTC AAG TGT      2112
```

-continued

```
Ala Glu Glu Gly Lys Ile Ala Glu Val Glu I le Ala Phe Phe Lys Cys
        690                 695                 700
CCG AAG TGT GGC CAT GTA GGG CCT GAA ACT C TC TGT CCC GAG TGT GGG          2160
Pro Lys Cys Gly His Val Gly Pro Glu Thr L eu Cys Pro Glu Cys Gly
705                 710                 715                 720
ATT AGG AAA GAG TTG ATA TGG ACA TGT CCC A AG TGT GGG GCT GAA TAC          2208
Ile Arg Lys Glu Leu Ile Trp Thr Cys Pro L ys Cys Gly Ala Glu Tyr
                    725                 730                 735
ACC AAT TCC CAG GCT GAG GGG TAC TCG TAT T CA TGT CCA AAG TGC AAT          2256
Thr Asn Ser Gln Ala Glu Gly Tyr Ser Tyr S er Cys Pro Lys Cys Asn
                740                 745                 750
GTG AAG CTA AAG CCA TTC ACA AAG AGG AAG A TA AAG CCC TCA GAG CTC          2304
Val Lys Leu Lys Pro Phe Thr Lys Arg Lys I le Lys Pro Ser Glu Leu
            755                 760                 765
TTA AAC AGG GCC ATG GAA AAC GTG AAG GTT T AT GGA GTT GAC AAG CTT          2352
Leu Asn Arg Ala Met Glu Asn Val Lys Val T yr Gly Val Asp Lys Leu
770                 775                 780
AAG GGC GTA ATG GGA ATG ACT TCT GGC TGG A AG ATT GCA GAG CCG CTG          2400
Lys Gly Val Met Gly Met Thr Ser Gly Trp L ys Ile Ala Glu Pro Leu
785                 790                 795                 800
GAG AAA GGT CTT TTG AGA GCA AAA AAT GAA G TT TAC GTC TTT AAG GAT          2448
Glu Lys Gly Leu Leu Arg Ala Lys Asn Glu V al Tyr Val Phe Lys Asp
                805                 810                 815
GGA ACC ATA AGA TTT GAT GCC ACA GAT GCT C CA ATA ACT CAC TTT AGG          2496
Gly Thr Ile Arg Phe Asp Ala Thr Asp Ala P ro Ile Thr His Phe Arg
            820                 825                 830
CCT AGG GAG ATA GGA GTT TCA GTG GAA AAG C TG AGA GAG CTT GGC TAC          2544
Pro Arg Glu Ile Gly Val Ser Val Glu Lys L eu Arg Glu Leu Gly Tyr
        835                 840                 845
ACC CAT GAC TTC GAA GGG AAA CCT CTG GTG A GT GAA GAC CAG ATA GTT          2592
Thr His Asp Phe Glu Gly Lys Pro Leu Val S er Glu Asp Gln Ile Val
850                 855                 860
GAG CTT AAG CCC CAA GAT GTA ATC CTC TCA A AG GAG GCT GGC AAG TAC          2640
Glu Leu Lys Pro Gln Asp Val Ile Leu Ser L ys Glu Ala Gly Lys Tyr
865                 870                 875                 880
CTC TTA AGA GTG GCC AGG TTT GTT GAT GAT C TT CTT GAG AAG TTC TAC          2688
Leu Leu Arg Val Ala Arg Phe Val Asp Asp L eu Leu Glu Lys Phe Tyr
                885                 890                 895
GGA CTT CCC AGG TTC TAC AAC GCC GAA AAA A TG GAG GAT TTA ATT GGT          2736
Gly Leu Pro Arg Phe Tyr Asn Ala Glu Lys M et Glu Asp Leu Ile Gly
            900                 905                 910
CAC CTA GTG ATA GGA TTG GCC CCT CAC ACT T CA GCC GGA ATC GTG GGG          2784
His Leu Val Ile Gly Leu Ala Pro His Thr S er Ala Gly Ile Val Gly
        915                 920                 925
AGG ATA ATA GGC TTT GTA GAT GCT CTG GTT G GC TAC GCT CAC CCC TAC          2832
Arg Ile Ile Gly Phe Val Asp Ala Leu Val G ly Tyr Ala His Pro Tyr
930                 935                 940
TTC CAT GCG GCC AAG AGA AGG AAC TGT GAT G GA GAT GAG GAT AGT GTA          2880
Phe His Ala Ala Lys Arg Arg Asn Cys Asp G ly Asp Glu Asp Ser Val
945                 950                 955                 960
ATG CTA CTC CTT GAT GCC CTA TTG AAC TTC T CC AGA TAC TAC CTC CCC          2928
Met Leu Leu Leu Asp Ala Leu Leu Asn Phe S er Arg Tyr Tyr Leu Pro
                965                 970                 975
GAA AAA AGA GGA GGA AAA ATG GAC GCT CCT C TT GTC ATA ACC ACG AGG          2976
Glu Lys Arg Gly Gly Lys Met Asp Ala Pro L eu Val Ile Thr Thr Arg
            980                 985                 990
CTT GAT CCA AGA GAG GTG GAC AGT GAA GTG C AC AAC ATG GAT GTC GTT          3024
Leu Asp Pro Arg Glu Val Asp Ser Glu Val H is Asn Met Asp Val Val
        995                 1000                1005
```

| | |
|---|---|
| AGA TAC TAT CCA TTA GAG TTC TAT GAA GCA A CT TAC GAG CTT AAA TCA<br>Arg Tyr Tyr Pro Leu Glu Phe Tyr Glu Ala T hr Tyr Glu Leu Lys Ser<br>    1010                       1015                1020 | 3072 |
| CCA AAG GAA CTT GTG AGA GTT ATA GAG GGA G TT GAA GAT AGA TTA GGA<br>Pro Lys Glu Leu Val Arg Val Ile Glu Gly V al Glu Asp Arg Leu Gly<br>1025                  103 0              1035             1040 | 3120 |
| AAG CCT GAA ATG TAT TAC GGA ATA AAG TTC A CC CAC GAT ACC GAC GAC<br>Lys Pro Glu Met Tyr Tyr Gly Ile Lys Phe T hr His Asp Thr Asp Asp<br>               1045                1050             1055 | 3168 |
| ATA GCT CTA GGA CCA AAG ATG AGC CTC TAC A AG CAG TTG GGA GAT ATG<br>Ile Ala Leu Gly Pro Lys Met Ser Leu Tyr L ys Gln Leu Gly Asp Met<br>    1060                       1065                1070 | 3216 |
| GAG GAG AAA GTG AAG AGG CAA TTG ACA TTG G CA GAG AGA ATT AGA GCT<br>Glu Glu Lys Val Lys Arg Gln Leu Thr Leu A la Glu Arg Ile Arg Ala<br>         1075                    1080             1085 | 3264 |
| GTG GAT CAA CAC TAT GTT GCT GAA ACA ATC C TC AAC TCC CAC TTA ATT<br>Val Asp Gln His Tyr Val Ala Glu Thr Ile L eu Asn Ser His Leu Ile<br>    1090                       1095                1100 | 3312 |
| CCC GAC TTG AGG GGT AAC CTA AGG AGC TTT A CT AGA CAA GAA TTT CGC<br>Pro Asp Leu Arg Gly Asn Leu Arg Ser Phe T hr Arg Gln Glu Phe Arg<br>1105                  111 0              1115             1120 | 3360 |
| TGT GTG AAG TGT AAC ACA AAG TAC AGA AGG C CG CCC TTG GAT GGA AAA<br>Cys Val Lys Cys Asn Thr Lys Tyr Arg Arg P ro Pro Leu Asp Gly Lys<br>         1125                    1130             1135 | 3408 |
| TGC CCA GTC TGT GGA GGA AAG ATA GTG CTG A CA GTT AGC AAA GGA GCC<br>Cys Pro Val Cys Gly Gly Lys Ile Val Leu T hr Val Ser Lys Gly Ala<br>               1140                1145             1150 | 3456 |
| ATT GAA AAG TAC TTG GGG ACT GCC AAG ATG C TC GTA GCT AAC TAC AAC<br>Ile Glu Lys Tyr Leu Gly Thr Ala Lys Met L eu Val Ala Asn Tyr Asn<br>               1155                1160             1165 | 3504 |
| GTA AAG CCA TAT ACA AGG CAG AGA ATA TGC T TG ACG GAG AAG GAT ATT<br>Val Lys Pro Tyr Thr Arg Gln Arg Ile Cys L eu Thr Glu Lys Asp Ile<br>    1170                       1175                1180 | 3552 |
| GAT TCA CTC TTT GAG TAC TTA TTC CCA GAA G CC CAG TTA ACG CTC ATT<br>Asp Ser Leu Phe Glu Tyr Leu Phe Pro Glu A la Gln Leu Thr Leu Ile<br>1185                  119 0              1195             1200 | 3600 |
| GTA GAT CCA AAC GAC ATC TGT ATG AAA ATG A TC AAG GAA AGA ACG GGG<br>Val Asp Pro Asn Asp Ile Cys Met Lys Met I le Lys Glu Arg Thr Gly<br>               1205                1210             1215 | 3648 |
| GAA ACA GTT CAA GGA GGC CTG CTT GAG AAC T TT AAT TCC TCT GGA AAT<br>Glu Thr Val Gln Gly Gly Leu Leu Glu Asn P he Asn Ser Ser Gly Asn<br>    1220                       1225                1230 | 3696 |
| AAT GGG AAG AAA ATA GAG AAG AAG GAG AAA A AG GCA AAG GAA AAG CCT<br>Asn Gly Lys Lys Ile Glu Lys Lys Glu Lys L ys Ala Lys Glu Lys Pro<br>         1235                    1240             1245 | 3744 |
| AAA AAG AAG AAA GTT ATA AGC TTG GAC GAC T TC TTC TCC AAA CGC<br>Lys Lys Lys Lys Val Ile Ser Leu Asp Asp P he Phe Ser Lys Arg<br>    1250                       1255                1260 | 3789 |

(2) INFORMATION FOR SEQ ID NO:4:

(i) SEQUENCE CHARACTERISTICS:
        (A) LENGTH: 1263 amino  acids
        (B) TYPE: amino acid
        (D) TOPOLOGY: linear (ii) MOLECULE TYPE: peptide (xi) SEQUENCE DESCRIPTION: SEQ ID NO:4:

Met Glu Leu Pro Lys Glu Ile Glu Glu Tyr P he Glu Met Leu Gln Arg
1               5                    10                 15

-continued

```
Glu Ile Asp Lys Ala Tyr Glu Ile Ala Lys Lys Ala Arg Ser Gln Gly
             20                  25                  30
Lys Asp Pro Ser Thr Asp Val Glu Ile Pro Gln Ala Thr Asp Met Ala
         35                  40                  45
Gly Arg Val Glu Ser Leu Val Gly Pro Pro Gly Val Ala Gln Arg Ile
     50                  55                  60
Arg Glu Leu Leu Lys Glu Tyr Asp Lys Glu Ile Val Ala Leu Lys Ile
 65                  70                  75                  80
Val Asp Glu Ile Ile Glu Gly Lys Phe Gly Asp Phe Gly Ser Lys Glu
                 85                  90                  95
Lys Tyr Ala Glu Gln Ala Val Arg Thr Ala Leu Ala Ile Leu Thr Glu
            100                 105                 110
Gly Ile Val Ser Ala Pro Leu Glu Gly Ile Ala Asp Val Lys Ile Lys
        115                 120                 125
Arg Asn Thr Trp Ala Asp Asn Ser Glu Tyr Leu Ala Leu Tyr Tyr Ala
    130                 135                 140
Gly Pro Ile Arg Ser Ser Gly Thr Ala Gln Ala Leu Ser Val Leu
145                 150                 155                 160
Val Gly Asp Tyr Val Arg Arg Lys Leu Gly Leu Asp Arg Phe Lys Pro
                165                 170                 175
Ser Gly Lys His Ile Glu Arg Met Val Glu Glu Val Asp Leu Tyr His
            180                 185                 190
Arg Ala Val Ser Arg Leu Gln Tyr His Pro Ser Pro Asp Glu Val Arg
        195                 200                 205
Leu Ala Met Arg Asn Ile Pro Ile Glu Ile Thr Gly Glu Ala Thr Asp
    210                 215                 220
Asp Val Glu Val Ser His Arg Asp Val Glu Gly Val Glu Thr Asn Gln
225                 230                 235                 240
Leu Arg Gly Gly Ala Ile Leu Val Leu Ala Glu Gly Val Leu Gln Lys
                245                 250                 255
Ala Lys Lys Leu Val Lys Tyr Ile Asp Lys Met Gly Ile Asp Gly Trp
            260                 265                 270
Glu Trp Leu Lys Glu Phe Val Glu Ala Lys Glu Lys Gly Glu Glu Ile
        275                 280                 285
Glu Glu Ser Glu Ser Lys Ala Glu Glu Ser Lys Val Glu Thr Arg Val
    290                 295                 300
Glu Val Glu Lys Gly Phe Tyr Tyr Lys Leu Tyr Glu Lys Phe Arg Ala
305                 310                 315                 320
Glu Ile Ala Pro Ser Glu Lys Tyr Ala Lys Glu Ile Ile Gly Gly Arg
                325                 330                 335
Pro Leu Phe Ala Gly Pro Ser Glu Asn Gly Gly Phe Arg Leu Arg Tyr
            340                 345                 350
Gly Arg Ser Arg Val Ser Gly Phe Ala Thr Trp Ser Ile Asn Pro Ala
        355                 360                 365
Thr Met Val Leu Val Asp Glu Phe Leu Ala Ile Gly Thr Gln Met Lys
    370                 375                 380
Thr Glu Arg Pro Gly Lys Gly Ala Val Val Thr Pro Ala Thr Thr Ala
385                 390                 395                 400
Glu Gly Pro Ile Val Lys Leu Lys Asp Gly Ser Val Val Arg Val Asp
                405                 410                 415
Asp Tyr Asn Leu Ala Leu Lys Ile Arg Asp Glu Val Glu Glu Ile Leu
            420                 425                 430
Tyr Leu Gly Asp Ala Ile Ile Ala Phe Gly Asp Phe Val Glu Asn Asn
```

-continued

|   |   |   | 435 |   |   |   | 440 |   |   |   | 445 |   |
|---|---|---|---|---|---|---|---|---|---|---|---|---|

Gln Thr Leu Leu Pro Ala Asn Tyr Val Glu Glu Trp Trp Ile Gln Glu
          450                  455              460

Phe Val Lys Ala Val Asn Glu Ala Tyr Glu Val Glu Leu Arg Pro Phe
465                  470                 475               480

Glu Glu Asn Pro Arg Glu Ser Val Glu Glu Ala Ala Glu Tyr Leu Glu
                485                 490               495

Val Asp Pro Glu Phe Leu Ala Lys Met Leu Tyr Asp Pro Leu Arg Val
          500                  505              510

Lys Pro Pro Val Glu Leu Ala Ile His Phe Ser Glu Ile Leu Glu Ile
     515                  520              525

Pro Leu His Pro Tyr Tyr Thr Leu Tyr Trp Asn Thr Val Asn Pro Lys
     530                  535              540

Asp Val Glu Arg Leu Trp Gly Val Leu Lys Asp Lys Ala Thr Ile Glu
545                  550                 555               560

Trp Gly Thr Phe Arg Gly Ile Lys Phe Ala Lys Lys Ile Glu Ile Ser
                565                 570               575

Leu Asp Asp Leu Gly Ser Leu Lys Arg Thr Leu Glu Leu Leu Gly Leu
                580                 585               590

Pro His Thr Val Arg Glu Gly Ile Val Val Val Asp Tyr Pro Trp Ser
     595                  600              605

Ala Ala Leu Leu Thr Pro Leu Gly Asn Leu Glu Trp Glu Phe Lys Ala
     610                  615              620

Lys Pro Phe Tyr Thr Val Ile Asp Ile Ile Asn Glu Asn Asn Gln Ile
625                  630                 635               640

Lys Leu Arg Asp Arg Gly Ile Ser Trp Ile Gly Ala Arg Met Gly Arg
                645                 650               655

Pro Glu Lys Ala Lys Glu Arg Lys Met Lys Pro Pro Val Gln Val Leu
          660                  665              670

Phe Pro Ile Gly Leu Ala Gly Gly Ser Ser Arg Asp Ile Lys Lys Ala
          675                  680              685

Ala Glu Glu Gly Lys Ile Ala Glu Val Glu Ile Ala Phe Phe Lys Cys
     690                  695              700

Pro Lys Cys Gly His Val Gly Pro Glu Thr Leu Cys Pro Glu Cys Gly
705                  710                 715               720

Ile Arg Lys Glu Leu Ile Trp Thr Cys Pro Lys Cys Gly Ala Glu Tyr
                725                 730               735

Thr Asn Ser Gln Ala Glu Gly Tyr Ser Tyr Ser Cys Pro Lys Cys Asn
                740                 745              750

Val Lys Leu Lys Pro Phe Thr Lys Arg Lys Ile Lys Pro Ser Glu Leu
          755                  760              765

Leu Asn Arg Ala Met Glu Asn Val Lys Val Tyr Gly Val Asp Lys Leu
     770                  775              780

Lys Gly Val Met Gly Met Thr Ser Gly Trp Lys Ile Ala Glu Pro Leu
785                  790                 795               800

Glu Lys Gly Leu Leu Arg Ala Lys Asn Glu Val Tyr Val Phe Lys Asp
                805                 810               815

Gly Thr Ile Arg Phe Asp Ala Thr Asp Ala Pro Ile Thr His Phe Arg
          820                  825              830

Pro Arg Glu Ile Gly Val Ser Val Glu Lys Leu Arg Glu Leu Gly Tyr
                835                 840               845

Thr His Asp Phe Glu Gly Lys Pro Leu Val Ser Glu Asp Gln Ile Val
850                  855                 860

```
Glu Leu Lys Pro Gln Asp Val Ile Leu Ser Lys Glu Ala Gly Lys Tyr
865                 870                 875                 880

Leu Leu Arg Val Ala Arg Phe Val Asp Leu Leu Glu Lys Phe Tyr
            885                 890                 895

Gly Leu Pro Arg Phe Tyr Asn Ala Glu Lys Met Glu Asp Leu Ile Gly
            900                 905                 910

His Leu Val Ile Gly Leu Ala Pro His Thr Ser Ala Gly Ile Val Gly
            915                 920                 925

Arg Ile Ile Gly Phe Val Asp Ala Leu Val Gly Tyr Ala His Pro Tyr
            930                 935                 940

Phe His Ala Ala Lys Arg Arg Asn Cys Asp Gly Asp Glu Asp Ser Val
945                 950                 955                 960

Met Leu Leu Leu Asp Ala Leu Leu Asn Phe Ser Arg Tyr Tyr Leu Pro
            965                 970                 975

Glu Lys Arg Gly Gly Lys Met Asp Ala Pro Leu Val Ile Thr Thr Arg
            980                 985                 990

Leu Asp Pro Arg Glu Val Asp Ser Glu Val His Asn Met Asp Val Val
            995                 1000                1005

Arg Tyr Tyr Pro Leu Glu Phe Tyr Glu Ala Thr Tyr Glu Leu Lys Ser
    1010                1015                1020

Pro Lys Glu Leu Val Arg Val Ile Glu Gly Val Glu Asp Arg Leu Gly
1025                1030                1035                1040

Lys Pro Glu Met Tyr Tyr Gly Ile Lys Phe Thr His Asp Thr Asp Asp
            1045                1050                1055

Ile Ala Leu Gly Pro Lys Met Ser Leu Tyr Lys Gln Leu Gly Asp Met
            1060                1065                1070

Glu Glu Lys Val Lys Arg Gln Leu Thr Leu Ala Glu Arg Ile Arg Ala
            1075                1080                1085

Val Asp Gln His Tyr Val Ala Glu Thr Ile Leu Asn Ser His Leu Ile
            1090                1095                1100

Pro Asp Leu Arg Gly Asn Leu Arg Ser Phe Thr Arg Gln Glu Phe Arg
1105                1110                1115                1120

Cys Val Lys Cys Asn Thr Lys Tyr Arg Arg Pro Pro Leu Asp Gly Lys
            1125                1130                1135

Cys Pro Val Cys Gly Gly Lys Ile Val Leu Thr Val Ser Lys Gly Ala
            1140                1145                1150

Ile Glu Lys Tyr Leu Gly Thr Ala Lys Met Leu Val Ala Asn Tyr Asn
            1155                1160                1165

Val Lys Pro Tyr Thr Arg Gln Arg Ile Cys Leu Thr Glu Lys Asp Ile
    1170                1175                1180

Asp Ser Leu Phe Glu Tyr Leu Phe Pro Glu Ala Gln Leu Thr Leu Ile
1185                1190                1195                1200

Val Asp Pro Asn Asp Ile Cys Met Lys Met Ile Lys Glu Arg Thr Gly
            1205                1210                1215

Glu Thr Val Gln Gly Gly Leu Leu Glu Asn Phe Asn Ser Ser Gly Asn
            1220                1225                1230

Asn Gly Lys Lys Ile Glu Lys Lys Glu Lys Lys Ala Lys Glu Lys Pro
            1235                1240                1245

Lys Lys Lys Lys Val Ile Ser Leu Asp Asp Phe Phe Ser Lys Arg
            1250                1255                1260
```

(2) INFORMATION FOR SEQ ID NO:5:

```
     (i) SEQUENCE CHARACTERISTICS:
         (A) LENGTH: 8450 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (xi) SEQUENCE DESCRIPTION: SEQ ID NO:5:

CATAACTAAA TTATTACATT TAGTTATATG GATGGGGGAA AAATTAACAA C ATGTGTTAT      60

GTTTCCTCTG GAAAATTGAT CTATAATAAT CTAGGAGCAC AATTTCCAAT G GAGGGTCAT     120

CAATGAACGA AGGTGAACAT CAAATAAAGC TTGACGAGCT ATTCGAAAAG T TGCTCCGAG     180

CTAGGAAGAT ATTCAAAAAC AAAGATGTCC TTAGGCATAG CTATACTCCC A AGGATCTAC     240

CTCACAGACA TGAGCAAATA GAAACTCTCG CCCAAATTTT AGTACCAGTT C TCAGAGGAG     300

AAACTCCATC AAACATATTC GTTTATGGGA AGACTGGAAC TGGAAAGACT G TAACTGTAA     360

AATTTGTAAC TGAAGAGCTG AAAAGAATAT CTGAAAAATA CAACATTCCA G TTGATGTGA     420

TCTACATTAA TTGTGAGATT GTCGATACTC ACTATAGAGT TCTTGCTAAC A TAGTTAACT     480

ACTTCAAAGA TGAGACTGGG ATTGAAGTTC CAATGGTAGG TTGGCCTACC G ATGAAGTTT     540

ACGCAAAGCT TAAGCAGGTT ATAGATATGA AGGAGAGGTT TGTGATAATT G TGTTGGATG     600

AAATTGACAA GTGGTAAAGA AGAGTGGTGA TGAGGTTCTC TATTCATTAA C AAGAATAAA     660

TACTGAACTT AAAAGGGCTA AAGTGAGTGT AATTGGTATA TCAAACGACC T TAAATTTAA     720

AGAGTATCTA GATCCAAGAG TTCTCTCAAG TTTGAGTGAG GAAGAGGTGG T ATTCCCACC     780

CTATGATGCA AATCAGCTTA GGGATATACT GACCCAAAGA GCTGAAGAGG C CTTTTATCC     840

TGGGGTTTTA GACGAAGGTG TGATTCCCCT CTGTGCAGCA TTAGCTGCTA G AGAGCATGG     900

AGATGCAAGA AAGGCACTTG ACCTTCTAAG AGTTGCAGGG GAAATAGCGG A AAGAGAAGG     960

GGCAAGTAAA GTAACTGAAA AGCATGTTTG GAAAGCCCAG GAAAAGATTG A ACAGGACAT    1020

GATGGAGGAG GTAATAAAAA CTCTACCCCT TCAGTCAAAA GTTCTCCTCT A TGCCATAGT    1080

TCTTTTGGAC GAAAACGGCG ATTTACCAGC AAATACTGGG GATGTTTACG C TGTTTATAG    1140

GGAATTGTGC GAGTACATTG ACTTGGAACC TCTCACCCAA AGAAGGATAA G TGATCTAAT    1200

TAATGAGCTT GACATGCTTG GAATAATAAA TGCAAAAGTT GTTAGTAAGG G GAGATATGG    1260

GAGGACAAAG GAAATAAGGC TTAACGTTAC CTCATATAAG ATAAGAAATG T GCTGAGATA    1320

TGATTACTCT ATTCAGCCCC TCCTCACAAT TTCCCTTAAG AGTGAGCAGA G GAGGTTGAT    1380

CTAATGGATG AATTTGTAAA ATCACTTCTA AAAGCTAACT ATCTAATAAC T CCCTCTGCC    1440

TACTATCTCT TGAGAGAATA CTATGAAAAA GGTGAATTCT CAATTGTGGA G CTGGTAAAA    1500

TTTGCAAGAT CAAGAGAGAG CTACATAATT ACTGATGCTT TAGCAACAGA A TTCCTTAAA    1560

GTTAAAGGCC TTGAACCAAT TCTTCCAGTG GAAACAAAGG GGGGTTTTGT T TCCACTGGA    1620

GAGTCCCAAA AAGAGCAGTC TTATGAAGAG TCTTTTGGGA CTAAAGAAGA A ATTTCCCAG    1680

GAGATTAAAG AAGGAGAGAG TTTTATTTCC ACTGGAAGTG AACCACTTGA A GAGGAGCTC    1740

AATAGCATTG GAATTGAGGA AATTGGGGCA AATGAAGAGT TAGTTTCTAA T GGAAATGAC    1800

AATGGTGGAG AGGCAATTGT CTTTGACAAA TATGGCTATC CAATGGTATA T GCTCCAGAA    1860

GAAATAGAGG TTGAGGAGAA GGAGTACTCG AAGTATGAAG ATCTGACAAT A CCCATGAAC    1920

CCCGACTTCA ATTATGTGGA AATAAAGGAA GATTATGATG TTGTCTTCGA T GTTAGGAAT    1980

GTAAAGCTGA AGCCTCCTAA GGTAAAGAAC GGTAATGGGA AGGAAGGTGA A ATAATTGTT    2040
```

```
GAAGCTTATG CTTCTCTCTT CAGGAGTAGG TTGAAGAAGT TAAGGAAAAT A CTAAGGGAA    2100

AATCCTGAAT TGGACAATGT TGTTGATATT GGGAAGCTGA AGTATGTGAA G GAAGATGAA    2160

ACCGTGACAA TAATAGGGCT TGTCAATTCC AAGAGGGAAG TGAATAAAGG A TTGATATTT    2220

GAAATAGAAG ATCTCACAGG AAAGGTTAAA GTTTTCTTGC CGAAAGATTC G GAAGATTAT    2280

AGGGAGGCAT TTAAGGTTCT TCCAGATGCC GTCGTCGCTT TTAAGGGGGT G TATTCAAAG    2340

AGGGGAATTT TGTACGCCAA CAAGTTTTAC CTTCCAGACG TTCCCCTCTA T AGGAGACAA    2400

AAGCCTCCAC TGGAAGAGAA AGTTTATGCT ATTCTCATAA GTGATATACA C GTCGGAAGT    2460

AAAGAGTTCT GCGAAAATGC CTTCATAAAG TTCTTAGAGT GGCTCAATGG A AACGTTGAA    2520

ACTAAGGAAG AGGAAGAAAT CGTGAGTAGG GTTAAGTATC TAATCATTGC A GGAGATGTT    2580

GTTGATGGTG TTGGCGTTTA TCCGGGCCAG TATGCCGACT TGACGATTCC A GATATATTC    2640

GACCAGTATG AGGCCCTCGC AAACCTTCTC TCTCACGTTC CTAAGCACAT A ACAATGTTC    2700

ATTGCCCCAG GAAACCACGA TGCTGCTAGG CAAGCTATTC CCAACCAGA A TTCTACAAA     2760

GAGTATGCAA AACCTATATA CAAGCTCAAG AACGCCGTGA TAATAAGCAA T CCTGCTGTA    2820

ATAAGACTAC ATGGTAGGGA CTTTCTGATA GCTCATGGTA GGGGATAGA G GATGTCGTT     2880

GGAAGTGTTC CTGGGTTGAC CCATCACAAG CCCGGCCTCC CAATGGTTGA A CTATTGAAG    2940

ATGAGGCATG TAGCTCCAAT GTTTGGAGGA AAGGTTCCAA TAGCTCCTGA T CCAGAAGAT    3000

TTGCTTGTTA TAGAAGAAGT TCCTGATGTA GTTCACATGG GTCACGTTCA C GTTTACGAT    3060

GCGGTAGTTT ATAGGGGAGT TCAGCTGGTT AACTCCGCCA CCTGGCAGGC T CAGACCGAG    3120

TTCCAGAAGA TGGTGAACAT AGTTCCAACG CCTGCAAAGG TTCCCGTTGT T GATATTGAT    3180

ACTGCAAAAG TTGTCAAGGT TTTGGACTTT AGTGGGTGGT GCTGATGGAG C TTCCAAAGG    3240

AAATTGAGGA GTATTTTGAG ATGCTTCAAA GGGAAATTGA CAAAGCTTAC G AGATTGCTA    3300

AGAAGGCTAG GAGTCAGGGT AAAGACCCCT CAACCGATGT TGAGATTCCC C AGGCTACAG    3360

ACATGGCTGG AAGAGTTGAG AGCTTAGTTG GCCCTCCCGG AGTTGCTCAG A GAATTAGGG    3420

AGCTTTTAAA AGAGTATGAT AAGGAAATTG TTGCTTTAAA GATAGTTGAT G AGATAATTG    3480

AGGGCAAATT TGGTGATTTT GGAAGTAAAG AGAAGTACGC TGAACAGGCT G TAAGGACAG    3540

CCTTGGCAAT ATTAACTGAG GGTATTGTTT CTGCTCCACT TGAGGGTATA G CTGATGTTA    3600

AAATCAAGCG AAACACCTGG GCTGATAACT CTGAATACCT CGCCCTTTAC T ATGCTGGGC    3660

CAATTAGGAG TTCTGGTGGA ACTGCTCAAG CTCTCAGTGT ACTTGTTGGT G ATTACGTTA    3720

GGCGAAAGCT TGGCCTTGAT AGGTTTAAGC CAAGTGGGAA GCATATAGAG A GAATGGTTG    3780

AGGAAGTTGA CCTCTATCAT AGAGCTGTTT CAAGGCTTCA ATATCATCCC T CACCTGATG    3840

AAGTGAGATT AGCAATGAGG AATATTCCCA TAGAAATCAC TGGTGAAGCC A CTGACGATG    3900

TGGAGGTTTC CCATAGAGAT GTAGAGGGAG TTGAGACAAA TCAGCTGAGA G GAGGAGCGA    3960

TCCTAGTTTT GGCGGAGGGT GTTCTCCAGA AGGCTAAAAA GCTCGTGAAA T ACATTGACA    4020

AGATGGGGAT TGATGGATGG GAGTGGCTTA AAGAGTTTGT AGAGGCTAAA G AAAAAGGTG    4080

AAGAAATCGA AGAGAGTGAA AGTAAAGCCG AGGAGTCAAA AGTTGAAACA A GGGTGGAGG    4140

TAGAGAAGGG ATTCTACTAC AAGCTCTATG AGAAATTTAG GGCTGAGATT G CCCCAAGCG    4200

AAAAGTATGC AAAGGAAATA ATTGGTGGGA GGCCGTTATT CGCTGGACCC T CGGAAAATG    4260

GGGGATTTAG GCTTAGATAT GGTAGAAGTA GGGTGAGTGG ATTTGCAACA T GGAGCATAA    4320

ATCCAGCAAC AATGGTTTTG GTTGACGAGT TCTTGGCCAT TGGAACTCAA A TGAAAACCG    4380
```

-continued

```
AGAGGCCTGG GAAAGGTGCA GTAGTGACTC CAGCAACAAC CGCTGAAGGG C CGATTGTTA    4440

AGCTAAAGGA TGGGAGTGTT GTTAGGGTTG ATGATTACAA CTTGGCCCTC A AAATAAGGG    4500

ATGAAGTCGA AGAGATACTT TATTTGGGAG ATGCAATCAT AGCCTTTGGA G ACTTTGTGG    4560

AGAACAATCA AACTCTCCTT CCTGCAAACT ATGTAGAGGA GTGGTGGATC C AAGAGTTCG    4620

TAAAGGCCGT TAATGAGGCA TATGAAGTTG AGCTTAGACC CTTTGAGGAA A ATCCCAGGG    4680

AGAGCGTTGA GGAAGCAGCA GAGTACCTTG AAGTTGACCC AGAATTCTTG G CTAAGATGC    4740

TTTACGATCC TCTAAGGGTT AAGCCTCCCG TGGAGCTAGC CATACACTTC T CGGAAATCC    4800

TGGAAATTCC TCTCCACCCA TACTACACCC TTTATTGGAA TACTGTAAAT C CTAAAGATG    4860

TTGAAAGACT TTGGGGAGTA TTAAAAGACA AGGCCACCAT AGAATGGGGC A CTTTCAGAG    4920

GTATAAAGTT TGCAAAGAAA ATTGAAATTA GCCTGGACGA CCTGGGAAGT C TTAAGAGAA    4980

CCCTAGAGCT CCTGGGACTT CCTCATACGG TAAGAGAAGG GATTGTAGTG G TTGATTATC    5040

CGTGGAGTGC AGCTCTTCTC ACTCCATTGG GCAATCTTGA ATGGGAGTTT A AGGCCAAGC    5100

CCTTCTACAC TGTAATAGAC ATCATTAACG AGAACAATCA GATAAAGCTC A GGGACAGGG    5160

GAATAAGCTG GATAGGGGCA AGAATGGGAA GGCCAGAGAA GGCAAAAGAA A GAAAAATGA    5220

AGCCACCTGT TCAAGTCCTC TTCCCAATTG GCTTGGCAGG GGGTTCTAGC A GAGATATAA    5280

AGAAGGCTGC TGAAGAGGGA AAAATAGCTG AAGTTGAGAT TGCTTTCTTC A AGTGTCCGA    5340

AGTGTGGCCA TGTAGGGCCT GAAACTCTCT GTCCCGAGTG TGGGATTAGG A AGAGTTGA     5400

TATGGACATG TCCCAAGTGT GGGGCTGAAT ACACCAATTC CCAGGCTGAG G GGTACTCGT    5460

ATTCATGTCC AAAGTGCAAT GTGAAGCTAA AGCCATTCAC AAAGAGGAAG A TAAAGCCCT    5520

CAGAGCTCTT AAACAGGGCC ATGGAAAACG TGAAGGTTTA TGGAGTTGAC A AGCTTAAGG    5580

GCGTAATGGG AATGACTTCT GGCTGGAAGA TTGCAGAGCC GCTGGAGAAA G GTCTTTTGA    5640

GAGCAAAAAA TGAAGTTTAC GTCTTTAAGG ATGGAACCAT AAGATTTGAT G CCACAGATG    5700

CTCCAATAAC TCACTTTAGG CCTAGGGAGA TAGGAGTTTC AGTGGAAAAG C TGAGAGAGC    5760

TTGGCTACAC CCATGACTTC GAAGGGAAAC CTCTGGTGAG TGAAGACCAG A TAGTTGAGC    5820

TTAAGCCCCA AGATGTAATC CTCTCAAAGG AGGCTGGCAA GTACCTCTTA A GAGTGGCCA    5880

GGTTTGTTGA TGATCTTCTT GAGAAGTTCT ACGGACTTCC CAGGTTCTAC A CGCCGAAA     5940

AAATGGAGGA TTTAATTGGT CACCTAGTGA TAGGATTGGC CCCTCACACT T CAGCCGGAA    6000

TCGTGGGGAG GATAATAGGC TTTGTAGATG CTCTGGTTGG CTACGCTCAC C CCTACTTCC    6060

ATGCGGCCAA GAGAAGGAAC TGTGATGGAG ATGAGGATAG TGTAATGCTA C TCCTTGATG    6120

CCCTATTGAA CTTCTCCAGA TACTACCTCC CCGAAAAAAG AGGAGGAAAA A TGGACGCTC    6180

CTCTTGTCAT AACCACGAGG CTTGATCCAA GAGAGGTGGA CAGTGAAGTG C ACAACATGG    6240

ATGTCGTTAG ATACTATCCA TTAGAGTTCT ATGAAGCAAC TTACGAGCTT A AATCACCAA    6300

AGGAACTTGT GAGAGTTATA GAGGGAGTTG AAGATAGATT AGGAAAGCCT G AAATGTATT    6360

ACGGAATAAA GTTCACCCAC GATACCGACG ACATAGCTCT AGGACCAAAG A TGAGCCTCT    6420

ACAAGCAGTT GGGAGATATG GAGGAGAAAG TGAAGAGGCA ATTGACATTG G CAGAGAGAA    6480

TTAGAGCTGT GGATCAACAC TATGTTGCTG AAACAATCCT CAACTCCCAC T TAATTCCCG    6540

ACTTGAGGGG TAACCTAAGG AGCTTTACTA GACAAGAATT TCGCTGTGTG A AGTGTAACA    6600

CAAAGTACAG AAGGCCGCCC TTGGATGGAA AATGCCCAGT CTGTGGAGGA A AGATAGTGC    6660

TGACAGTTAG CAAAGGAGCC ATTGAAAAGT ACTTGGGGAC TGCCAAGATG C TCGTAGCTA    6720

ACTACAACGT AAAGCCATAT ACAAGGCAGA GAATATGCTT GACGGAGAAG G ATATTGATT    6780
```

```
CACTCTTTGA GTACTTATTC CCAGAAGCCC AGTTAACGCT CATTGTAGAT C CAAACGACA    6840

TCTGTATGAA AATGATCAAG GAAAGAACGG GGGAAACAGT TCAAGGAGGC C TGCTTGAGA    6900

ACTTTAATTC CTCTGGAAAT AATGGGAAGA AAATAGAGAA GAAGGAGAAA A AGGCAAAGG    6960

AAAAGCCTAA AAAGAAGAAA GTTATAAGCT TGGACGACTT CTTCTCCAAA C GCTGACCAC    7020

AACTTTTAAG TTCTTTCTTG AGAATAAATT CCCAGGTGGC TTAGAGAATG A AGATTGTGT    7080

GGTGTGGTCA TGCCTGCTTC TTGGTGGAGG ATAGGGGGAC TAAGATACTA A TCGATCCAT    7140

ACCCAGACGT TGATGAAGAC AGAATAGGCA AGGTCGATTA CATTCTAGTT A CCCACGAGC    7200

ACATGGATCA CTACGGTAAG ACCCCACTAA TAGCAAAGCT CAGTGATGCC G AGGTTATAG    7260

GGCCGAAAAC AGTTTATCTC ATGGCAATAA GTGATGGGCT AACAAAGGTC A GAGAGATAG    7320

AGGTGGGACA GGAAATCGAG CTGGGAGATA TTAGGGTTAG GGCATTTTTC A CAGAGCATC    7380

CAACAAGCCA GTATCCCCTG GGATATCTAA TTGAAGGAAG CAAAGAGTG G CTCACTTGG     7440

GAGATACATA CTACAGTCCA GCTTTTACAG AGTTGAGGGG AAAGGTTGAT G TTCTTTTGG    7500

TTCCAATAGG TGGGAAGTCC ACCGCTAGTG TAAGGGAGGC TGCGGATATA G TGGAGATGA    7560

TAAGGCCCAG GATAGCAGTT CCAATGCACT ATGGAACGTA CAGCGAGGCC G ATCCTGAAG    7620

AGTTCAAGAA GGAGCTCCAA AAAAGGCGCA TATGGGTTTT AGTAAAGGAT C TTAAGCCCT    7680

ATGAGGGTTT TGAAATCTGA AGGTGTTTCA ATGCTAAATA CTGAGCTCTT A ACCACTGGA    7740

GTCAAGGGGT TAGATGAGCT TTTAGGTGGT GGAGTTGCTA AGGGAGTAAT A CTCCAAGTT    7800

TACGGGCCAT TTGCCACCGG GAAGACAACT TTTGCAATGC AGGTTGGATT A TTGAATGAG    7860

GGAAAAGTGG CTTATGTTGA TACTGAGGGG GGATTCTCCC CCGAAAGGTT A GCTCAAATG    7920

GCAGAATCAA GGAACTTGGA TGTGGAGAAA GCACTTGAAA AGTTCGTGAT A TTCGAACCT    7980

ATGGATTTAA ACGAGCAAAG ACAGGTAATT GCGAGGTTGA AAAATATCGT G AATGAAAAG    8040

TTTTCTTTAG TTGTGGTCGA CTCCTTTACG GCCCATTATA GAGCGGAGGG G AGTAGAGAG    8100

TATGGAGAAC TTTCCAAGCA ACTCCAAGTT CTTCAGTGGA TTGCCAGAAG A AAAAACGTT    8160

GCCGTTATAG TTGTCAATCA AGTTTATTAC GATTCAAACT CAGGAATTCT T AAACCAATA    8220

GCTGAGCACA CCCTGGGGTA CAAAACAAAG GACATCCTCC GCTTTGAAAG G CTTAGGGTT    8280

GGAGTGAGAA TTGCAGTTCT GGAAAGGCAT AGGTTTAGGC CAGAGGGTGG G ATGGTATAC    8340

TTCAAAATAA CAGATAAAGG ATTGGAGGAT GTAAAAAACG AAGATTAGAG C CTGTCGTAG    8400

ACCTCCTGGG CAATCCTCAG CGTTGCCTTA TAGAGCTTCT CACTAATAAT             8450

(2) INFORMATION FOR SEQ ID NO:6:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(iii) HYPOTHETICAL: NO (xi) SEQUENCE DESCRIPTION: SEQ ID NO:6:

CCGGAACCGC CTCCCTCAGA GCCGCCACCC TCAGAACCGC CACCC                     45

(2) INFORMATION FOR SEQ ID NO:7:

(i) SEQUENCE CHARACTERISTICS:
```

(A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic RNA"

(iii) HYPOTHETICAL: NO (xi) SEQUENCE DESCRIPTION: SEQ ID NO:7:

GUUUUCCCAG UCACGAC                                                    17

(2) INFORMATION FOR SEQ ID NO:8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(iii) HYPOTHETICAL: NO (xi) SEQUENCE DESCRIPTION: SEQ ID NO:8:

GATGAGTTCG TGTCCGTACA ACT                                             23

(2) INFORMATION FOR SEQ ID NO:9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(iii) HYPOTHETICAL: NO (xi) SEQUENCE DESCRIPTION: SEQ ID NO:9:

ACAAAGCCAG CCGGAATATC TG                                              22

(2) INFORMATION FOR SEQ ID NO:10:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(iii) HYPOTHETICAL: NO (xi) SEQUENCE DESCRIPTION: SEQ ID NO:10:

TACAATACGA TGCCCCGTTA AG                                              22

(2) INFORMATION FOR SEQ ID NO:11:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

-continued (iii) HYPOTHETICAL: NO (xi) SEQUENCE DESCRIPTION: SEQ ID NO:11:

CAGAGGAGGT TGATCCCATG GATGAATTTG TA                32

(2) INFORMATION FOR SEQ ID NO:12:

(i) SEQUENCE CHARACTERISTICS:
      (A) LENGTH: 32 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "synthetic DNA"

(iii) HYPOTHETICAL: NO (xi) SEQUENCE DESCRIPTION: SEQ ID NO:12:

TTTAGTGGGT GGTGCCCATG GAGCTTCCAA AG                32

DNA POLYMERASE

This application is the national phase under 35 U.S.C. §371 of prior PCT International Application No. PCT/JP96/03869 which has an International filing date of Dec. 26, 1996 which designated the United States of America, the entire contents of which are hereby incorporated by reference.

TECHNICAL FIELD

The present invention relates a DNA polymerase which is useful as a reagent for genetic engineering, a method for producing the same, and a gene encoding thereof.

BACKGROUND ART

DNA polymerases are useful enzymes as reagents for genetic engineering, and the DNA polymerases are widely used for method of determining base sequences of DNA, labeling, methods of site-directed mutagenesis, and the like. Also, thermostable DNA polymerases have recently been remarked with the development of the polymerase chain reaction (PCR) method, and various DNA polymerases suitable for the PCR method have been developed and commercialized.

Presently known DNA polymerases can be roughly classified into four families according to amino acid sequence homologies, among which family A (pol I type enzymes) and family B ($\alpha$ type enzymes) account for the great majority. Although DNA polymerases belonging to each family generally possess mutually similar biochemical properties, detailed comparison reveals that individual DNA polymerase enzymes differ from each other in terms of substrate specificity, substrate analog incorporation, degree and rate for primer extension, mode of DNA synthesis, association of exonuclease activity, optimum reaction conditions of temperature, pH and the like, and sensitivity to inhibitors. Thus, those possessing especially suitable properties for the respective experimental procedures have been selectively used of all available DNA polymerases.

DISCLOSURE OF INVENTION

An object of the present invention is to provide a novel DNA polymerase not belonging to any of the above families, and possessing biochemical properties not owned by any of the existing DNA polymerases. For example, primer extension activity and $3' \rightarrow 5'$ exonuclease activity are considered as mutually opposite properties, and none of the existing DNA polymerase enzymes with strong primer extension activity possess $3' \rightarrow 5'$ exonuclease activity, which is an important proofreading function for DNA synthesis accuracy. Also, the existing DNA polymerases possessing excellent proofreading functions are poor in primer extension activity. Therefore, development of a DNA polymerase possessing both potent primer extension activity and potent $3' \rightarrow 5'$ exonuclease activity would significantly contribute to DNA synthesis in vitro.

Another object of the present invention is to provide a method for producing the novel DNA polymerase mentioned above.

A still another object of the present invention is to provide a gene encoding the DNA polymerase of the present invention.

As a result of extensive investigation, the present inventors have found genes of the novel DNA polymerase from hyperthermophilic arcaebacterium *Pyrrococcus furious*, followed by cloning of the above genes, and have clarified that two kinds of novel proteins possess a novel DNA polymerase activity exhibiting the activity under coexistence of the above two kinds of proteins. Furthermore, the present inventors have prepared a transformant into which the above genes are introduced, and have succeeded in mass-producing the complex type DNA polymerase.

Accordingly, the gist of the present invention is as follows:

[1] A DNA polymerase characterized in that the DNA polymerase possesses the following properties:
  1) exhibiting higher polymerase activity when assayed by using as a substrate a complex resulting from primer annealing to a single stranded template DNA, as compared to the case where an activated DNA is used as a substrate;
  2) possessing a $3' \rightarrow 5'$ exonuclease activity;
  3) being capable of amplifying a DNA fragment of about 20 kbp, in the case where polymerase chain reaction (PCR) is carried out using $\lambda$-DNA as a template under the following conditions:
  PCR Conditions:
    (a) a composition of reaction mixture: containing 10 mM Tris-HCl (pH 9.2), 3.5 mM $MgCl_2$, 75 mM KCl, 400 $\mu$M each of dATP, dCTP, dGTP and dTTP, 0.01% bovine serum albumin, 0.1% Triton X-100, 5.0 ng/50 $\mu$l $\lambda$-DNA, 10 pmole/50 $\mu$l primer $\lambda$1 (SEQ ID NO:8 in Sequence Listing), primer $\lambda$11 (SEQ ID NO:9 in Sequence Listing), and 3.7 units/50 $\mu$l DNA polymerase;
    (b) reaction conditions: carrying out a 30-cycle PCR, wherein one cycle is defined as at 98° C. for 10 seconds and at 68° C. for 10 minutes;
[2] The DNA polymerase according to the above item [1], characterized in that the DNA polymerase exhibits a lower error rate in DNA synthesis as compared to Taq DNA polymerase;
[3] The DNA polymerase according to the above item [1] or [2], wherein the molecular weight as determined by gel filtration method is about 220 kDa or about 385 kDa;
[4] The DNA polymerase according to any one of the above items [1] to [3], characterized in that the DNA polymerase exhibits an activity under coexistence of two kinds of DNA polymerase-constituting protein, a first DNA polymerase-constituting protein and a second DNA polymerase-constituting protein;
[5] The DNA polymerase according to the above item [4], characterized in that the molecular weights of the first DNA polymerase-constituting protein and the second DNA polymerase-constituting protein are about 90,000 Da and about 140,000 Da as determined by SDS-PAGE, respectively;
[6] The DNA polymerase according to the above item [4] or [5], characterized in that the first DNA polymerase-constituting protein which constitutes the DNA polymerase according to the above item [4] or [5] comprises the amino acid sequence as shown by SEQ ID NO:2 in Sequence Listing, or is a functional equivalent thereof possessing substantially the same activity which results from deletion, insertion, addition or substitution of one or more amino acids in the amino acid sequence;
[7] The DNA polymerase according to the above item [4] or [5], characterized in that the second DNA polymerase-constituting protein which constitutes the DNA polymerase according to the above item [4] or [5] comprises the amino acid sequence as shown by SEQ ID NO:4 in Sequence Listing, or is a functional equivalent thereof possessing substantially the same activity which results from deletion, insertion, addition or substitution of one or more amino acids in the amino acid sequence;

[8] The DNA polymerase according to item [4] or [5], characterized in that the first DNA polymerase-constituting protein which constitutes the DNA polymerase according to the above item [4] or [5] comprises the amino acid sequence as shown by SEQ ID NO:2 in Sequence Listing, or is a functional equivalent thereof possessing substantially the same activity which results from deletion, insertion, addition or substitution of one or more amino acids in the amino acid sequence, and that the second DNA polymerase-constituting protein which constitutes the DNA polymerase according to the above item [4] or [5] comprises the amino acid sequence as shown by SEQ ID NO:4 in Sequence Listing, or is a functional equivalent thereof possessing substantially the same activity which results from deletion, insertion, addition or substitution of one or more amino acids in the amino acid sequence;

[9] A first DNA polymerase-constituting protein which constitutes the DNA polymerase according to the above item [4] or [5], wherein the first DNA polymerase-constituting protein comprises the amino acid sequence as shown by SEQ ID NO:2, or an amino acid sequence resulting from deletion, insertion, addition or substitution of one or more amino acids in the amino acid sequence, as a functional equivalent thereof possessing substantially the same activity;

[10] A second DNA polymerase-constituting protein which constitutes the DNA polymerase according to the above [4] or [5], wherein the second DNA polymerase-constituting protein comprises the amino acid sequence as shown by SEQ ID NO:4, or an amino acid sequence resulting from deletion, insertion, addition or substitution of one or more amino acids in the amino acid sequence as a functional equivalent thereof possessing substantially the same activity;

[11] A DNA containing a base sequence encoding the first DNA polymerase-constituting protein according to the above item [9], characterized in that the DNA comprises an entire sequence of a base sequence encoding the amino acid sequence as shown by SEQ ID NO:2 in Sequence Listing, or a partial sequence thereof, or that the DNA encodes a protein having an amino acid sequence resulting from deletion, insertion, addition or substitution of one or more amino acids in the amino acid sequence of SEQ ID NO:2 and possessing a function as the first DNA polymerase-constituting protein;

[12] A DNA containing a base sequence encoding the first DNA polymerase-constituting protein according to the above items [9], characterized in that the DNA comprises an entire sequence of the base sequence as shown by SEQ ID NO:1 in Sequence Listing or a partial sequence thereof, or that the DNA comprises a base sequence capable of hybridizing thereto under stringent conditions;

[13] A DNA containing a base sequence encoding the second DNA polymerase-constituting protein according to the above item [10], characterized in that the DNA comprises an entire sequence of a base sequence encoding the amino acid sequence as shown by SEQ ID NO:4, or a partial sequence thereof, or that the DNA encodes a protein having an amino acid sequence resulting from deletion, insertion, addition or substitution of one or more amino acids in the amino acid sequence of SEQ ID NO:4 and possessing a function as the second DNA polymerase-constituting protein;

[14] A DNA containing a base sequence encoding the second DNA polymerase-constituting protein according to the item [10], characterized in that the DNA comprises an entire sequence of the base sequence as shown by SEQ ID NO:4 in Sequence Listing or a partial sequence thereof, or that the DNA comprises a base sequence capable of hybridizing thereto under stringent conditions;

[15] A method for producing a DNA polymerase, characterized in that the method comprises culturing a transformant containing both gene encoding the first DNA polymerase-constituting protein according to the above item [11] or [12], and gene encoding the second DNA polymerase-constituting protein according to the above item [13] or [14], and collecting the DNA polymerase from the resulting culture; and

[16] A method for producing a DNA polymerase, characterized in that the method comprises culturing a transformant containing gene encoding the first DNA polymerase-constituting protein according to the above item [11] or [12], and a transformant containing gene encoding the second DNA polymerase-constituting protein according to the above item [13] or [14], separately; mixing DNA polymerase-constituting proteins contained in the resulting culture; and collecting the DNA polymerase.

Figure 1:
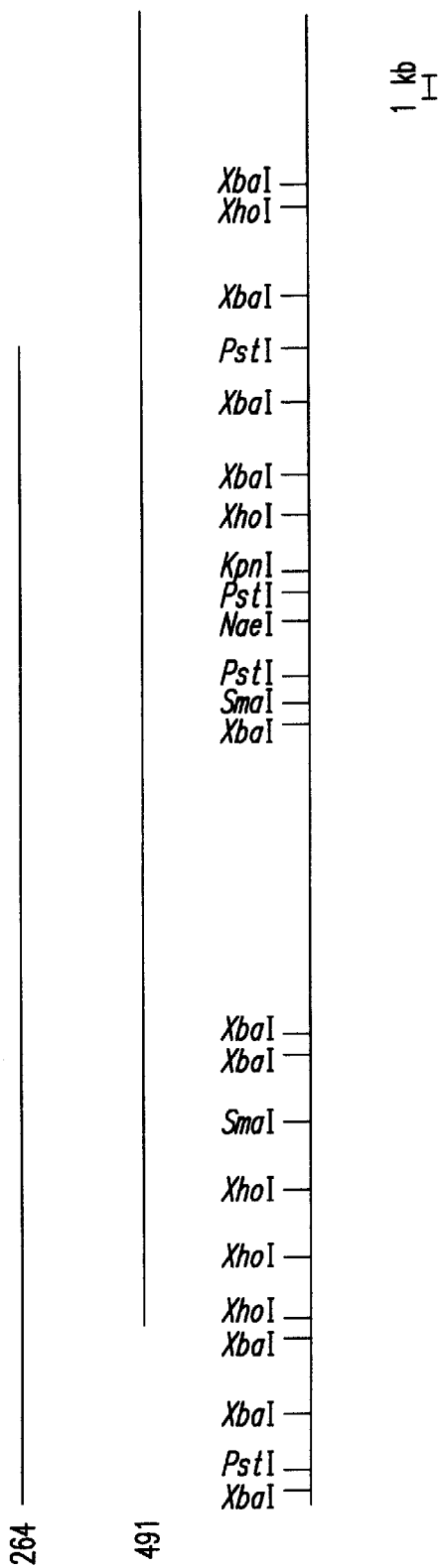
FIG. 1 shows a restriction endonuclease map of the DNA fragment inserted into the cosmid Clone No. 264 and the cosmid Clone No. 491 obtained in Example 1.

BEST MODE FOR CARRYING OUT THE INVENTION (1) DNA Polymerase of Present Invention and Constituting Proteins Thereof An example of the DNA polymerase of the present invention has the following properties:

1) exhibiting higher polymerase activity when assayed by using as a substrate a complex resulting from primer annealing to a single stranded template DNA, as compared to the case where an activated DNA (DNase I-treated calf thymus DNA) is used as a substrate;
2) possessing a 3'→5' exonuclease activity;
3) optimum pH being between 6.5 and 7.0 (in potassium phosphate buffer, at 75° C.);
4) exhibiting a remaining activity of about 80% after heat treatment at 80° C. for 30 minutes;
5) being capable of amplifying a DNA fragment of about 20 kbp, in the case where polymerase chain reaction (PCR) is carried out using λ-DNA as a template under the following conditions:
   PCR conditions:
   (a) composition of reaction mixture: containing 10 mM Tris-HCl (pH 9.2), 3.5 mM $MgCl_2$, 75 mM KCl, 400 μM each of dATP, dCTP, dGTP and dTTP, 0.01% bovine serum albumin (BSA), 0.1% Triton X-100, 5.0 ng/50 μl λ-DNA, 10 pmole/50 μl primer λ1 (SEQ ID NO:0:8 in Sequence Listing), primer λ11 (SEQ ID NO:9 in Sequence Listing), and 3.7 units/50 μl DNA polymerase. Here, one unit of the DNA polymerase is defined as follows: Fifty microliters of a reaction mixture [20 mM Tris-HCl (pH 7.7), 15 mM $MgCl_2$, 2 mM 2-mercaptoethanol, 0.2 mg/ml activated DNA, 40 μM each of dATP, dCTP, dGTP and dTTP, 60 nM [$^3$H]-dTTP (manufactured by Amersham)], containing a sample to assay activity, is reacted at 75° C. for 15 minutes. A 40 μl portion of this reaction mixture is spotted onto a DE paper (manufactured by Whatman) and washed with 5% $Na_2HPO_4$ five times. Thereafter, the remaining radioactivity on the DE paper is measured using a liquid scintillation counter, and the amount of the enzyme causing the incorporation of 10 nmol of [$^3$H]-dTMP per 30 minutes into a substrate DNA is defined as one unit of the enzyme; and (b) PCR conditions: carrying out a 30-cycle PCR, wherein one cycle is defined as at 98° C. for 10 seconds and at 68° C. for 10 minutes; and 6) The DNA polymerase of the present invention is superior to the Taq DNA polymerase in terms of both primer extension activity and accuracy of DNA synthesis. Specifically, the DNA polymerase of the present invention is superior to the Taq DNA polymerase, a typical thermostable DNA polymerase (e.g., TaKaRa Taq, manufactured by Takara Shuzo Co., Ltd.), in terms of primer extension properties in DNA synthesis reaction, for instance, DNA strand length capable of DNA amplification by PCR method, and accuracy of DNA synthesis reaction (low error rate in DNA synthesis).

The DNA polymerase of the present invention is an enzyme constituted by two kinds of proteins, wherein a molecular weight of the DNA polymerase of the present invention is about 220 kDa or about 385 kDa, as determined by gel filtration, and also shown by two bands corresponding to about 90,000 Da and about 140,000 Da on SDS-PAGE, respectively. The protein of about 90,000 Da (corresponding to ORF3 as described below) is herein referred to as the first DNA polymerase-constituting protein, and the protein of about 140,000 Da (corresponding to ORF4 as described below) is herein referred to as the second DNA polymerase-constituting protein. It is assumed that in the DNA polymerase of the present invention, the first DNA polymerase-constituting protein and the second DNA polymerase-constituting protein are non-covalently bonded to form a complex in a molar ratio of 1:1 or 1:2.

The first DNA polymerase-constituting protein which constitutes the DNA polymerase of the present invention may comprise the amino acid sequence shown by SEQ ID NO:2 in Sequence Listing, or may be a functional equivalent possessing substantially the same activity. Also, the second DNA polymerase-constituting protein may comprise the amino acid sequence shown by SEQ ID NO:4 in Sequence Listing, or may be a functional equivalent possessing substantially the same activity.

The term "a functional equivalent" as described in the present specification is defined as follows. A protein existing in nature can undergo mutation, such as deletion, insertion, addition and substitution, of amino acids in an amino acid sequence thereof owing to modification reaction and the like of the protein itself in vivo or during purification, besides causation such as polymorphism and mutation of the genes encoding it. However, it has been known that there are some proteins which exhibit substantially the same physiological activities or biological activities as a protein without mutation. Those proteins having structural differences as described above without recognizing any significant differences of the functions and the activities thereof, are referred to as "a functional equivalent." Here, the number of mutated amino acids is not particularly limited, as long as the resulting protein exhibits substantially the same physiological activities or biological activities as a protein without mutation. Examples thereof include one or more of mutations, for instance, one or several mutations, more specifically one to about ten mutations (such as deletion, insertion, addition and substitution) and the like.

The same can be said for the resulting proteins in the case where the above mutation is artificially introduced into the amino acid sequence of a protein. In this case, more diverse mutants can be prepared. For example, although the methionine residue at the N-terminus of a protein expressed in *Escherichia coli* is reportedly often removed by the action of methionine aminopeptidase, since the methionine residue is not removed perfectly depending on the kinds of proteins, those having methionine residue and those without methionine residue can be both produced. However, the presence or absence of the methionine residue does not affect protein activity in most cases. It is also known that a polypeptide resulting from substitution of a particular cysteine residue with serine in the amino acid sequence of human interleukin 2 (IL-2) retains IL-2 activity [*Science*, 224, 1431 (1984)].

In addition, during the production of a protein by genetic engineering, the desired protein is often expressed as a fusion protein. For example, purification of the desired protein is facilitated by adding the N-terminal peptide chain derived from another protein to the N-terminus of the desired protein to increase the amount of expression of the desired protein, or by adding an appropriate peptide chain to the N- or C-terminus of the desired protein, expressing the protein, and using a carrier having affinity for the peptide chain added. Accordingly, a DNA polymerase having an amino acid sequence which has a partial difference with that of the DNA polymerase of the present invention is within the scope of the present invention as "a functional equivalent," as long as it exhibits substantially the same activities as the DNA polymerase of the present invention.

(2) Gene of DNA Polymerase of Present Invention

The DNA encoding the first DNA polymerase-constituting protein which constitutes the DNA polymerase of the present invention includes a DNA comprising an entire sequence of the base sequence encoding the amino acid sequence as shown by SEQ ID NO:2 in Sequence Listing or a partial sequence thereof including, for instance, a DNA comprising an entire sequence of the base sequence as shown by SEQ ID NO:1 or a partial sequence thereof. Specifically, a DNA comprising a partial sequence of the base sequence encoding the amino acid sequence as shown by SEQ ID NO:1 including, for instance, the DNA comprising a partial sequence of the base sequence as shown by SEQ ID NO:1 in Sequence Listing, the base sequence encoding a protein possessing a function of the first DNA polymerase-constituting protein is also included in the scope of the present invention. Also, in the amino acid sequence as shown by SEQ ID NO:2, the above DNA also includes a DNA encoding a protein comprising an amino acid sequence resulting from deletion, insertion, addition, substitution and the like of one or several amino acids, the protein possessing a function of the first DNA polymerase-constituting protein. Furthermore, a base sequence capable of hybridizing to the above base sequences under the stringent conditions, the base sequence encoding a protein possessing a function of the first DNA polymerase-constituting protein, is also included in the scope of the present invention. In addition, the DNA encoding the second DNA polymerase-constituting protein which constitutes the DNA polymerase of the present invention includes a DNA comprising an entire sequence of the base sequence encoding the amino acid sequence as shown by SEQ ID NO:3 in Sequence Listing or a partial sequence thereof including, for instance, a DNA comprising an entire sequence of the base sequence as shown by SEQ ID NO:3 in Sequence Listing or a partial sequence thereof. Specifically, the DNA comprising a partial sequence of the base sequence encoding the amino acid sequence as shown by SEQ ID NO:4, for instance, the DNA comprising a partial sequence of the base sequence as shown by SEQ ID NO:3 in Sequence Listing, the base sequence encoding a protein possessing a function of the second DNA polymerase-constituting protein, is also included in the scope of the present invention. Also, in the amino acid sequence as shown by SEQ ID NO:4, the above DNA also includes a DNA encoding a protein comprising an amino acid sequence resulting from deletion, insertion, addition, substitution and the like of one or several amino acids, the protein possessing a function of the second DNA polymerase-constituting protein. Furthermore, a base sequence capable of hybridizing to the above base sequences under the stringent conditions, the base sequence encoding a protein possessing a function of the second DNA polymerase-constituting protein, is also included in the scope of the present invention.

The term "protein possessing a function of the first DNA polymerase-constituting protein" or "protein possessing a function of the second DNA polymerase-constituting protein" herein refers to a protein possessing properties exhibiting a DNA polymerase activity with various physicochemical properties shown in the above items 1) to 6).

Here, the term "capable of hybridizing under the stringent conditions" refer to hybridizing to a probe, after incubating at 50° C. for 12 to 20 hours in 6×SSC (wherein 1×SSC shows 0.15 M NaCl, 0.015 M sodium citrate, pH 7.0) containing 0.5% SDS, 0.1% bovine serum albumin (BSA), 0.1% polyvinyl pyrrolidone, 0.1% Ficol 400, and 0.01% denatured salmon sperm DNA with the probe.

The term "DNA containing a base sequence encoding an amino acid sequence" described in the present specification will be explained. One to six kinds are known to exist for each amino acid with regards to a codon (triplet base combination) for designating a particular amino acid on the gene. Therefore, there can be a large number of DNA encoding an amino acid sequence, though depending on the amino acid sequence. In nature, genes do not always exist in stable forms, and it is not rare for genes to undergo mutations on a base sequence. There may be a case where mutations on the base sequence do not give rise to any changes in an amino acid sequence to be encoded (referred to as silent mutation). In this case, it can be said that different kinds of genes encoding the same amino acid sequence have been generated. The possibility, therefore, cannot be negated for producing a variety of genes encoding the same amino acid sequence after many generations of the organism even when a gene encoding a particular amino acid sequence is isolated.

Moreover, it is not difficult to artificially produce a variety of genes encoding the same amino acid sequence by means of various genetic engineering techniques. For example, when a codon used in the natural gene encoding the desired protein is used at a low frequency in the host in the production of the protein by genetic engineering, the amount of a protein expressed is sometimes low. In this case, high expression of the desired protein is achieved by artificially converting the codon into another one used at a high frequency in the host without changing the amino acid sequence encoded (for instance, Japanese Patent Laid-Open No. Hei 7-102146). As described above, it is, of course, possible to artificially produce a variety of genes encoding a particular amino acid sequence. Such artificially produced different polynucleotides are, therefore, included in the scope of the present invention, as long as the gene encodes the amino acid sequence disclosed in the present invention.

(3) Method for Producing DNA Polymerase of Present Invention

The present inventors have found genes of a novel DNA polymerase from a hyperthermophilic archaebacterium, *Pyrococcus furiosus*, and cloned to clarify that the genes encode a novel DNA polymerase exhibiting its activity by the coexistence of two kinds of proteins on the genes. In the present invention, the DNA polymerase of the present invention can be mass-produced by preparing transformants incorporating the above genes. For this purpose, the transformant may be prepared by a process comprising culturing a transformant containing both the gene encoding the first DNA polymerase-constituting protein and the gene encoding the second DNA polymerase-constituting protein, and collecting the DNA polymerase from the resulting culture. Alternatively, the transformant may be prepared by a process comprising separately culturing a transformant containing the gene encoding the first DNA polymerase-constituting protein and a transformant containing the gene encoding the second DNA polymerase-constituting protein, mixing the DNA polymerase-constituting proteins contained in the resulting culture, and collecting the DNA polymerase therefrom.

Here, the phrase "transformant containing both the gene encoding the first DNA polymerase-constituting protein and the gene encoding the second DNA polymerase-constituting protein" may be a transformant resulting from co-transformation with two expression vectors containing the respective genes, or it may be a transformant prepared by recombining both genes into one expression vector to allow the respective proteins to be expressed.

(4) A Cloning of the Genes of the DNA Polymerase of the Present Invention, an Analysis of Obtained Clones, Physicochemical Properties, Activities, Applicabilities to PCR Method of Expression Product DNA Polymerase, and the Like are Hereinafter Described in Detail.

The strain used for the present invention is not subject to particular limitation. Examples thereof include *Pyrococcus furiousus* DSM3638, as a strain belonging to the genus Pyrococcus. The above strain can be made available from Deutsche Sammlung von Mikroorganismen und Zellkulturen GmbH. In the case of culturing the above strain in an appropriate growth culture, preparing a crude extract from the resulting culture, and subjecting the crude extract to a polyacrylamide gel electrophoresis, since the present inventors found existences of several kinds of protein bands showing DNA polymerase activity in the gel, it has been anticipated that the genes corresponding to these respective bands have existed. Specifically, the novel DNA polymerase gene and the product thereof can be cloned by the procedures exemplified below.

1) DNA is extracted from *Pyrococcus furiousus;*
2) The DNA obtained in 1) is digested with an appropriate restriction endonuclease, to prepare a DNA library with a plasmid, cosmid and the like, as a vector;
3) The library prepared in 2) is introduced into *Escherichia coli*, and a foreign gene is expressed to prepare a protein library in which crude extracts of the resulting clones are collected;

4) A DNA polymerase activity is assayed by using the protein library prepared in 3), and a foreign DNA is taken out from the *Escherichia coli* clone which provides a crude extract having an activity;

5) The *Pyrococcus furiousus* DNA fragment contained in the plasmid or cosmid taken out is analyzed to narrow down the gene region encoding a protein exhibiting a DNA polymerase activity;

6) The base sequence of the region in which the protein exhibiting a DNA polymerase activity is presumably encoded is determined to deduce the primary structure of the protein; and 7) An expression plasmid is constructed to take a form which more easily allows the expression of the protein deduced in 6) in *Escherichia coli,* and the produced protein is purified and analyzed for the properties thereof.

The above DNA donor, *Pyrococcus furiousus* DSM3638, is a hyperthermophilic archaebacterium, which is cultured at 95° C. under anaerobic conditions. Known methods can be used as a method for disrupting grown cells followed by extracting and purifying DNA, a method for digesting the obtained DNA with a restriction endonuclease and for other methods. Such methods are described in detail by in *Molecular Cloning: A Laboratory Manual,* 75–178, published by Cold Spring Harbor Laboratory in 1982, edited by T. Maniatis et al.

In the preparation of a DNA library, the triple helix cosmid vector (manufactured by Stratagene), for example, can be used. The DNA of *Pyrococcus furiousus* is partially digested with Sau3AI (manufactured by Takara Shuzo Co., Ltd.), and the digested DNA is subjected to density gradient centrifugation to obtain the long DNA fragments. They are ligated to the BamHI site of the above vector, followed by in vitro packaging. The respective transformants obtained from the DNA library thus prepared are separately cultured. After harvesting, cells are disrupted by ultrasonication, and the resulting disruption is heat-treated to inactivate the DNA polymerase from the host *Escherichia coli.* Thereafter, a supernatant containing a thermostable protein can be obtained by centrifugation. The above supernatant is named as a cosmid protein library. By means of assaying the DNA polymerase activity using a portion of the supernatant, a clone that expresses the DNA polymerase derived from *Pyrococcus furiousus* can be obtained. DNA polymerase activity can be assayed using the known method described in *DNA Polymerase from Escherichia coli,* published by Harpar and Row, edited by D. R. Davis, 263–276 (authored by C. C. Richardson).

One of the DNA polymerase genes of *Pyrococcus furiosus* has already been cloned and its structure clarified by the present inventors, as described in *Nucleic Acids Research,* 21, 259–265 (1993). The translation product of the above gene is a polypeptide having a molecular weight of about 90,000 Da and consisting of 775 amino acids, and the amino acid sequence thereof clearly contains preserved sequences of the α-type DNA polymerases. In fact, since the DNA polymerase activity exhibited by this gene product is inhibited by aphidicolin, which is a specific inhibitor of α-type DNA polymerases, the above DNA polymerase is distinguishable from the DNA polymerase of the present invention. Therefore, the above known gene out of the obtained clones exhibiting thermostable DNA polymerase activity can be removed by a process comprising digesting the cosmid contained in each clone, carrying out hybridization with the above gene as a probe, and selecting an unhybridizing clone. A restriction endonuclease map of the DNA insert can be prepared for the cosmid digested with the resulting clone containing the novel DNA polymerase gene. Next, a location of the DNA polymerase gene on the above DNA fragment can be determined by a process comprising dividing the above DNA fragment into various regions on the basis of the obtained restriction endonuclease map, subcloning each region into a plasmid vector, introducing the resulting vector into *Escherichia coli,* and assaying the thermostable DNA polymerase activity exhibited therein. An XbaI-XbaI DNA fragment of about 10 kbp containing the DNA polymerase gene can be thus obtained.

The recombinant *Escherichia coli* harboring a plasmid incorporating the above DNA fragment exhibits a sufficient level of a DNA synthesis activity in the crude extract thereof even after treatment at 90° C. for 20 minutes, while such an activity is not found in any plasmids without incorporating a DNA fragment. Therefore, it can be concluded that the information for producing a thermostable polymerase is present on the DNA fragment, and that a gene having the above information is expressed in the above *Escherichia coli.* The plasmid resulting from recombination of the DNA fragment into a pTV118N vector (manufactured by Takara Shuzo Co., Ltd.) is named as pFU1001. The *Escherichia coli* JM109 transformed with the above plasmid is named and identified as *Escherichia coli* JM109/pFUFU1001, has been deposited under accession number FERM BP-5579 with the National Institute of Bioscience and Human-Technology, Agency of Industrial Science and Technology, Ministry of International Trade and Industry, of which the address is 1-3, Higashi 1-chome, Tsukuba-shi, Ibaraki-ken, 305, Japan, since Aug. 11, 1995 (date of original deposit) under the Budapest Treaty.

The base sequence of the DNA fragment inserted in the plasmid pFUFU1001 can be determined by a conventional method, for instance, by the dideoxy method. Furthermore, regions capable of encoding a protein in the base sequence, i.e., open reading frames (ORFs), can be deduced by analyzing the resulting base sequence.

Figure 2:
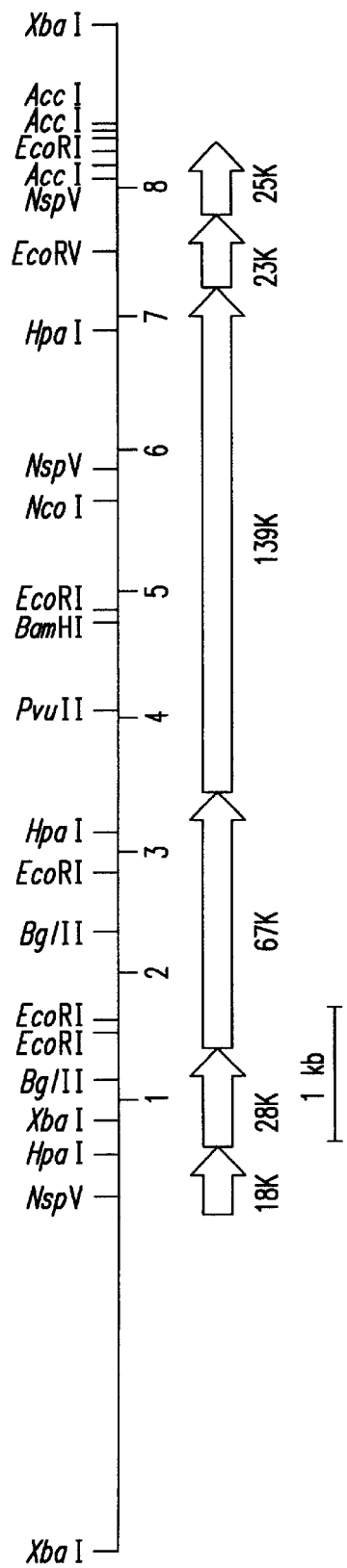
FIG. 2 shows a restriction endonuclease map of an XbaI-XbaI DNA fragment inserted into a plasmid pFU1001.

An 8,450 bp sequence in the base sequence of the XbaI-XbaI DNA fragment of about 10 kbp inserted in the plasmid pFU1001 is shown by SEQ ID NO:5 in Sequence Listing. In the base sequence, there are six consecutive ORFs, named as ORF1, ORF2, ORF3, ORF4, ORF5, and ORF6, respectively, naming from the 5' terminal side. FIG. 2 shows the restriction endonuclease map of the above XbaI-XbaI fragment and the location of the ORFs on the fragment (ORF1 to ORF6, from the left in the Figure).

A sequence showing homologies to any of known DNA polymerases was not found in any one of the above six ORFs. It should be noted, however, that on ORF1 and ORF2, there is a sequence homologous to the CDC6 protein found in *Saccharomyces cerivisiae,* or a sequence homologous to the CDC18 protein found in *Schizosaccharomyces pombe.* The CDC6 and the CDC18 are anticipated as proteins that are necessary for the cell cycle shift to the DNA synthesis phase (S phase) in yeasts, the proteins regulating initiation of the DNA replication. Also, the ORF6 has a sequence homologous to the RAD51 protein, known to act in DNA damage repair in yeasts and recombination in the somatic mitosis phase and in the meiosis phase in yeasts, and a sequence homologous to the Dmcl protein, a meiosis phase-specific homolog to the RAD51 protein. The gene encoding the RAD51 protein is also known to be expressed at the cell cycle shift from the G1 to S phase. For the other ORFs, namely ORF3, ORF4, and ORF5, there have been no known proteins found to have a homologous sequence.

It is possible to determine from which of the above ORFs the thermostable DNA polymerase activity is derived by a process comprising preparing recombinant plasmids inserted with the respective DNA fragments deleting various regions, transforming a host with the plasmids, and assaying the thermostable polymerase activity of each transformant obtained. The transformant resulting from transformation with a recombinant plasmid inserted with a DNA fragment prepared by deleting ORF1 or ORF2, or deleting ORF5 or ORF6, from the above XbaI-XbaI DNA fragment of about 10 kbp retains the thermostable DNA polymerase activity, while those resulting from transformation with a recombinant plasmid inserted with a DNA fragment prepared by deleting ORF3 or ORF4 loses its activity. This fact predicts that the DNA polymerase activity is encoded by ORF3 or ORF4.

It is possible to determine by which of ORF3 and ORF4 the DNA polymerase is encoded by a process comprising preparing recombinant plasmids separately inserted with the respective ORFs, transforming a host with each recombinant plasmid, and assaying exhibition of a thermostable DNA polymerase activity in each transformant obtained. Unexpectedly, only very weak DNA polymerase activity is detected in a crude extract obtained from the transformant containing ORF3 or ORF4 alone. However, since a similar level of a thermostable DNA polymerase activity to that in the transformant containing both ORF3 and ORF4 can be obtained in the case where the two extracts are mixed, it is shown that the novel DNA polymerase of the present invention requires the actions of the translation products of the two ORFs. It is possible to find out whether the two proteins form a complex to exhibit the DNA polymerase activity, or one modifies the other to convert it to an active enzyme by determining the molecular weight of the DNA polymerase. The results of the determination of the molecular weight of the above DNA polymerase by gel filtration method demonstrate that the above two proteins form a complex.

The base sequence of ORF3 is shown by SEQ ID NO:1 in Sequence Listing, and the amino acid sequence of the ORF3-derived translation product, namely the first DNA polymerase-constituting protein as deduced from the base sequence, is shown by SEQ ID NO:2. The base sequence of ORF4 is shown by SEQ ID NO:3 in Sequence Listing, and the amino acid sequence of the ORF4-derived translation product, namely the second DNA polymerase-constituting protein as deduced from the base sequence, is shown by SEQ ID NO:4.

The DNA polymerase of the present invention can be expressed in cells by culturing a transformant resulting from transformation with a recombinant plasmid into which both ORF3 and ORF4 are introduced, for instance, *Escherichia coli* JM109/pFUFU1001, under usual culturing conditions, for instance, culturing in an LB medium (10 g/l trypton, 5 g/l yeast extract, 5 g/l NaCl, pH 7.2) containing 100 µg/ml ampicillin. The above polymerase can be purified from the above cultured cells to the extent that only the two kinds of bands of nearly two kinds of the DNA polymerase-constituting proteins are obtained in SDS-polyacrylamide gel electrophoresis (SDS-PAGE), by carrying out ultrasonication, heat treatment, and chromatography using an anionic exchange column (RESOURCE Q column, manufactured by Pharmacia), a heparin Sepharose column (HiTrap Heparin, manufactured by Pharmacia), a gel filtration column (Superose 6HR, manufactured by Pharmacia) or the like. It is also possible to obtain the desired DNA polymerase by a process comprising separately culturing transformants respectively containing ORF3 or ORF4 alone as described above, and subsequently mixing the cultured cells obtained, their crude extracts, or purified DNA polymerase-constituting proteins. When mixing the two kinds of DNA polymerase-constituting proteins, special procedures are not required, and the DNA polymerase possessing an activity can be obtained simply by mixing the extracts from the respective transformants or the two proteins purified therefrom in appropriate amounts.

The DNA polymerase of the present invention thus obtained provides two bands at positions corresponding to molecular weights of about 90,000 Da and about 140,000 Da on the SDS-PAGE, and these two bands corresponding to the first and second DNA polymerase-constituting proteins, respectively.

Figure 3:
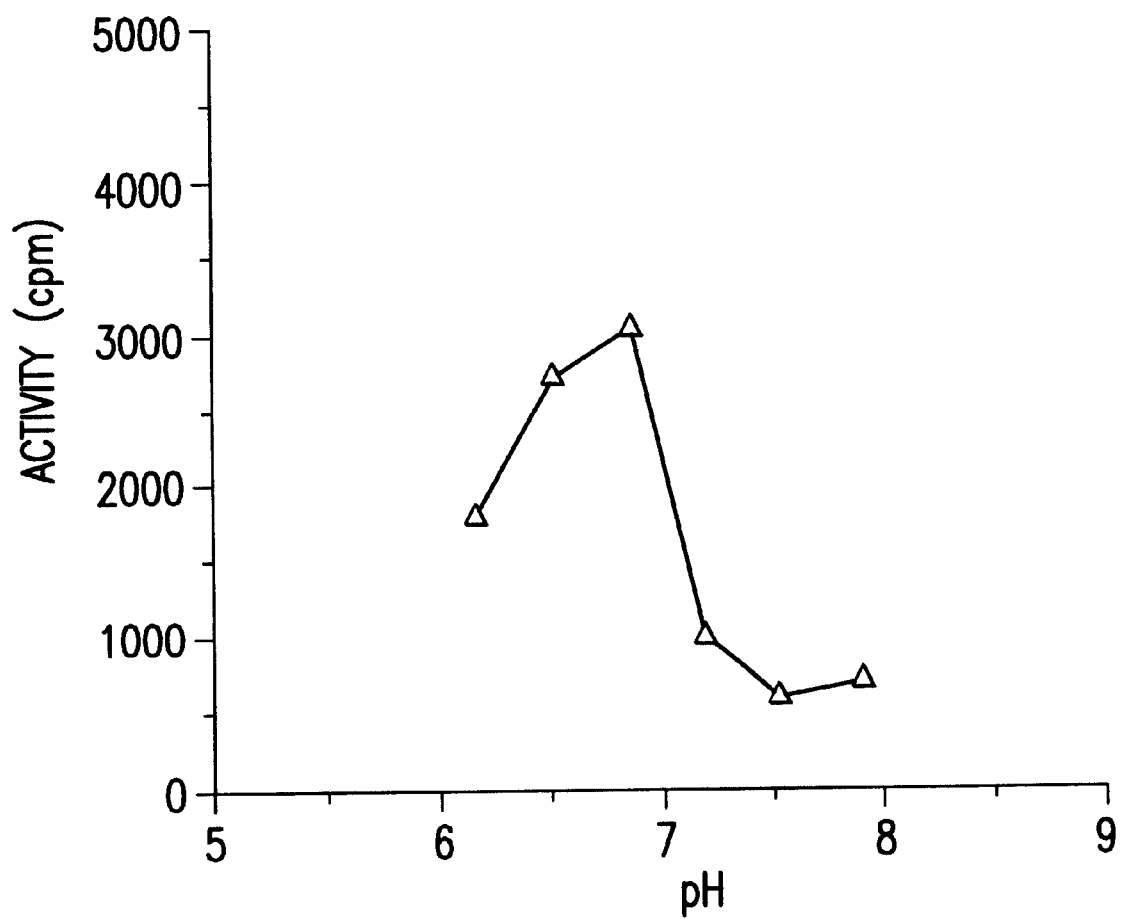
FIG. 3 is a graph for an optimum pH of the DNA polymerase of the present invention.
Figure 4:
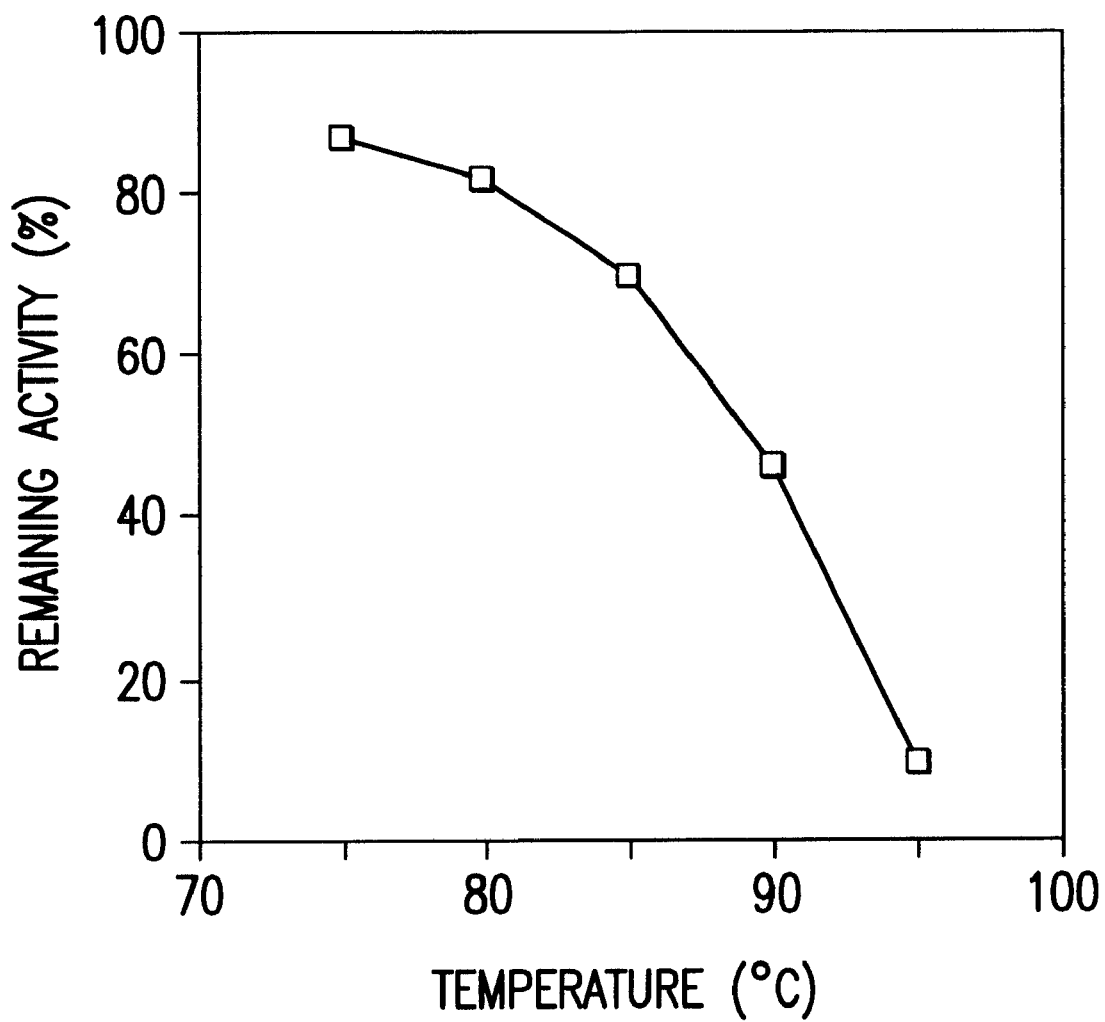
FIG. 4 is a graph for a heat stability of the DNA polymerase of the present invention.

As shown in FIG. 3, the DNA polymerase of the present invention exhibits the optimum pH is in the neighborhood of 6.5 to 7.0 at 75° C. in a potassium phosphate buffer. When an enzyme activity of the above DNA polymerase is assayed at various temperatures, the enzyme exhibits a high activity at 75° to 80° C. However, because the double stranded structure of the activated DNA used as a substrate for activity assay is destructed at higher temperatures, an accurate optimum temperature for the activity of the above enzyme has not been assayed. The above DNA polymerase possesses a high heat stability, retaining not less than 80% of the remaining activity even after a heat treatment at 80° C. for 30 minutes, as shown in FIG. 4. This level of the heat stability allows the use of the above enzyme for PCR method. Also, when assessing the influence of aphidicolin, a specific inhibitor of α-type DNA polymerases, it is demonstrated that the activity of the above DNA polymerase is not inhibited even in the presence of 2 mM aphidicolin.

Figure 6:
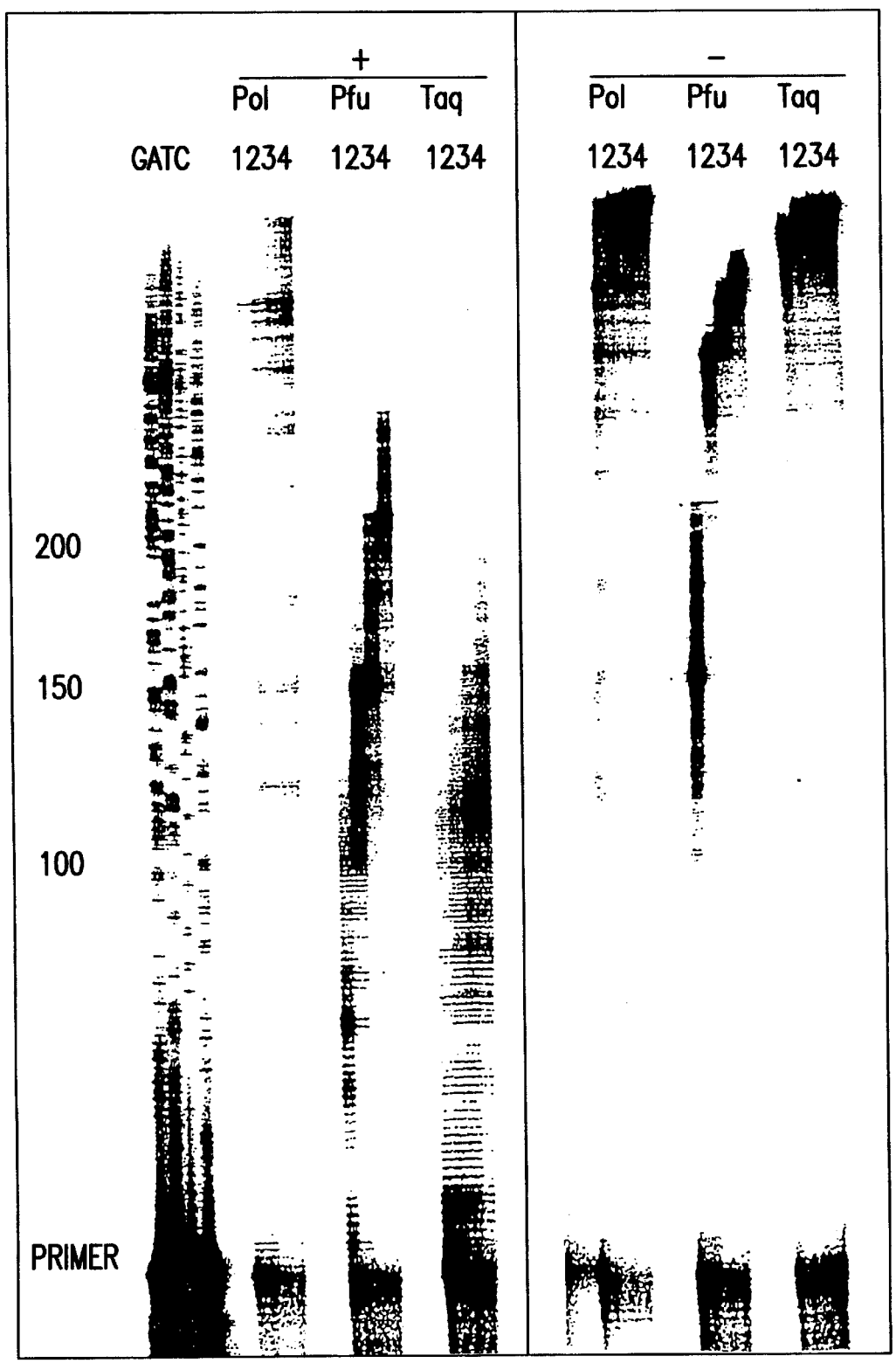
FIG. 6 is an autoradiogram for a primer extension activity of the DNA polymerase of the present invention.

As a result of analyzing the biochemical properties of the purified DNA polymerase, the DNA polymerase of the present invention possesses very excellent primer extension activity in vitro. As shown in Table 1, in the case where DNA polymerase activity is assayed using a substrate in a form resulting from primer annealing to a single stranded DNA (the M13-HT Primer), higher nucleotide incorporating activity as compared to that of the activated DNA used for usual activity assaying (DNase I-treated calf thymus DNA) can be demonstrated. When the primer extension ability of the DNA polymerase of the present invention is compared with that of other DNA polymerases using the above M13-HT Primer substrate, the DNA polymerase of the present invention exhibits superior extension activity as compared to known DNA polymerases derived from *Pyrococcus furiousus* (Pfu DNA polymerase, manufactured by Stratagene) and Taq DNA polymerase derived from *Thermus aquaticus* (TaKaRa Taq, manufactured by Takara Shuzo Co., Ltd.). Furthermore, when an activated DNA is added to this reaction system as a competitor substrate, the primer extension activities of the above two kinds of DNA polymerases are strongly inhibited, while that of the DNA polymerase of the present invention is inhibited at a low level, demonstrating that the DNA polymerase of the present invention possesses a high affinity for substrates of the primer extension type (FIG. 6).

TABLE 1

| Substrates | Relative Activity | | |
| --- | --- | --- | --- |
| | DNA Polymerase of the Present Invention | Pfu DNA Polymerase | Taq DNA Polymerase |
| activated DNA | 100 | 100 | 100 |
| thermal-denatured DNA | 340 | 87 | 130 |

TABLE 1-continued

| | Relative Activity | | |
| --- | --- | --- | --- |
| Substrates | DNA Polymerase of the Present Invention | Pfu DNA Polymerase | Taq DNA Polymerase |
| M13-HT primer | 170 | 23 | 90 |
| M13-RNA primer | 52 | 0.49 | 38 |
| poly dA-Oligo dT | 94 | 390 | 290 |
| poly A-Oligo dT | 0.085 | — | 0.063 |

Also, the DNA polymerase of the present invention shows excellent performance when used for the PCR method. In the DNA polymerase derived from *Thermus aquaticus*, commonly used for the PCR method, it is difficult to amplify a DNA fragment of not less than 10 kbp using, the above DNA polymerase alone, and a DNA fragment of not less than 20 kbp can be amplified when used in combination with another DNA polymerase [*Proceedings of the National Academy of Sciences of the USA*, 91, 2216–2220 (1994)]. Also, the strand length of DNA amplifiable using the Pfu DNA polymerase is reportedly at most about 3 kbp. By contrast, when using the DNA polymerase of the present invention, the amplification of a DNA fragment of 20 kbp in length is made possible even when used alone without addition of any other enzymes.

Figure 5:
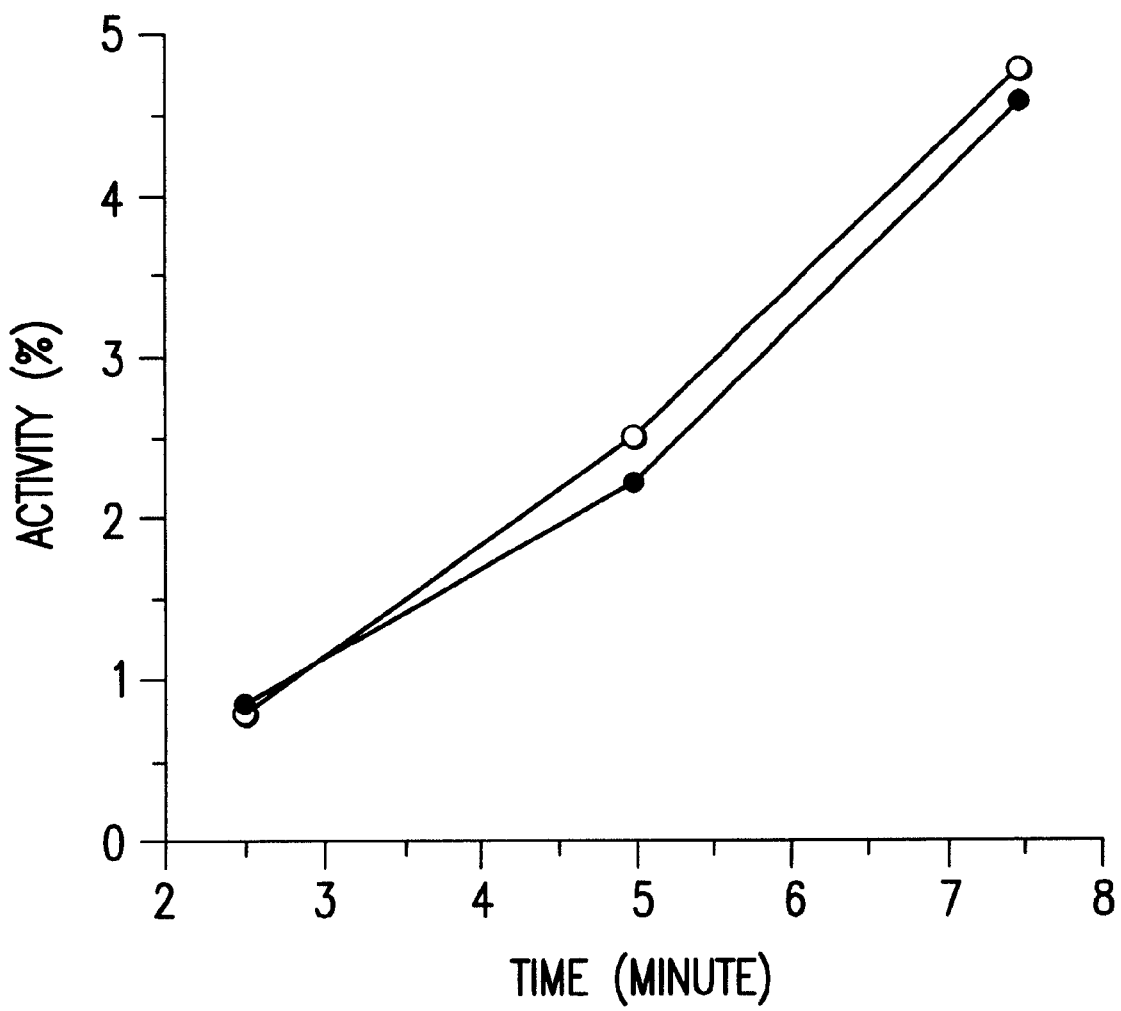
FIG. 5 is a graph for a 3'→5' exonuclease activity of the DNA polymerase of the present invention.

Moreover, the DNA polymerase of the present invention which also has associated 3'→51' exonuclease activity is comparable to the Pfu DNA polymerase, known to ensure very high accuracy in DNA synthesis, owing to its high activity in terms of the ratio of the exonuclease activity to the DNA polymerase activity (FIG. 5). Also, the error rate during the DNA synthesis reaction is lower for the DNA polymerase of the present invention than that of the Taq DNA polymerase. The various properties demonstrate that the DNA polymerase of the present invention serves very excellently as a reagent for genetic engineering techniques such as the PCR method.

The finding of the novel DNA polymerase genes according to the present invention also provides an interesting suggestion as follows. In order to determine the manner in which the region containing the genes for ORF3 and ORF4 encoding a novel DNA polymerase is intracellularly transcribed, the present inventors have analyzed an RNA fraction prepared from *Pyrococcus furiousus* cells by northern blotting method, RT-PCR method and primer extension method. As a result, it is confirmed that ORF1 to ORF6 are transcribed from immediately upstream of ORF1 as a single messenger RNA (mRNA). From the above finding, there is an expectation that the production of the ORF1 and the ORF2 in cells is subjected to the same control as that for the ORF3 and the ORF4. When considering in combination with the sequence homologies of ORF1, ORF2, ORF5, and ORF6 to those of CDC6 and CDC18, the CDC6 and the CDC18 being involved in the regulation for initiation of the DNA replication in yeasts, the above expectation suggests that the novel DNA polymerase of the present invention is highly likely to be a DNA polymerase important for the DNA replication. Since it is also expected that the DNA replication system of archaebacteria, to which group *Pyrococcus furiousus* belongs, is closely related to that of eukaryotic cells, there is a possibility of the presence of an enzyme similar to the DNA polymerase of the present invention as a DNA. polymerase important for replication that has not been found in eukaryotes.

It is also expected that thermostable DNA polymerases similar to the DNA polymerase of the present invention are produced in other bacteria belonging to hyperthermophilic archaebacteria like *Pyrococcus furiousus*, including, for instance, bacteria other than *Pyrococcus furiousus* belonging to the genus Pyrococcus; bacteria belonging to the genus Pyrodictium; the genus Thermococcus, the genus Staphylothermus, and other genera. When these enzymes are constituted by two DNA polymerase-constituting proteins, like the DNA polymerase of the present invention, it is expected that a similar DNA polymerase activity is exhibited by combining one of the two DNA polymerase-constituting proteins and the DNA polymerase-constituting protein of the present invention corresponding to the other DNA polymerase-constituting protein.

The thermostable DNA polymerases similar to the DNA polymerase of the present invention, produced by the above hyperthermophilic archaebacteria, are expected to have homology to the DNA polymerase of the present invention in terms of its amino acid sequence and the base sequence of the gene encoding thereof. It is therefore possible to obtain the gene for a thermostable DNA polymerase similar to the DNA polymerase of the present invention of which the base sequence is not identical to that of the DNA polymerase of the present invention but possesses similar enzyme activities by a process comprising introducing into an appropriate microorganism a DNA fragment obtained from one of the above thermophilic archaebacteria by hybridization using, as a probe, a gene isolated by the present invention or a portion of the above base sequence, and assaying the DNA polymerase activity in a heat-treated lysate prepared in the same manner as the above cosmid protein library by an appropriate method.

The above hybridization can be carried out under the following conditions. Specifically, a DNA-immobilized membrane is incubated with a probe at 50° C. for 12 to 20 hours in 6×SSC, wherein 1×SSC indicates 0.15 M NaCl, 0.015 M sodium citrate, pH 7.0, containing 0.5% SDS, 0.1% bovine serum albumin, 0.1% polyvinyl pyrrolidone, 0.1% Ficol 400, and 0.01% denatured salmon sperm DNA. After termination of the incubation, the membrane is washed, initiating at 37° C. in 2×SSC containing 0.5% SDS, and changing the SSC concentration to 0.1×SSC from the starting level, while varying the SSC temperature to 50° C. until the signal from the immobilized DNA becomes distinguishable from the background.

Thus, it is possible to obtain a gene for a thermostable DNA polymerase similar to the DNA polymerase of the present invention of which the DNA polymerase activity is not identical but of the same level as that of the DNA polymerase of the present invention, by introducing into an appropriate microorganism a DNA fragment obtained by a gene amplification reaction using, as a primer, a gene isolated by the present invention or a portion of the base sequence of the gene, with a DNA obtained from one of the above thermophilic archaebacteria as a template, or a DNA fragment resulting from the thermophilic archaebacterium by hybridization with the fragment obtained by a gene amplification reaction as a probe, and assaying the DNA polymerase activity in the same manner as above.

The present invention is hereinafter described by means of the following examples, but the scope of the present invention is not limited only to those examples. The % values shown in Examples below mean % by weight.

EXAMPLE 1

(1) Preparation of *Pyrococcus furiosus* Genomic DNA

*Pyrococcus furiousus* DSM3638 was cultured in the following manner:

A medium having a composition comprising 1% trypton, 0.5% yeast extract, 1% soluble starch, 3.5% Jamarin S Solid (Jamarin Laboratory), 0.5% Jamarin S Liquid (Jamarin Laboratory), 0.003% $MgSO_4$, 0.001% NaCl, 0.0001% $FeSO_4.7H_2O$, 0.0001% $CoSO_4$, 0.0001% $CaCl_2.7H_2O$, 0.0001% $ZnSO_4$, 0.1 ppm $CuSO_4.5H_2O$, 0.1 ppm $KAl(SO_4)_2$, 0.1 ppm $H_3BO_3$, 0.1 ppm $Na_2MoO_4.2H_2O$, and 0.25 ppm $NiCl_2.6H_2O$ was placed in a two-liter medium bottle and sterilized at 120° C. for 20 minutes. After removal of dissolved oxygen by sparging with nitrogen gas thereinto, the above strain was inoculated into the resulting medium. Thereafter, the medium was cultured by kept standing at 95° C. for 16 hours. After termination of the cultivation, cells were harvested by centrifugation.

The harvested cells were then suspended in 4 ml of 0.05 M Tris-HCl (pH 8.0) containing 25% sucrose. To this suspension, 0.8 ml of lysozyme [5 mg/ml, 0.25 M Tris-HCl (pH 8.0)] and 2 ml of 0.2 M EDTA were added and incubated at 20° C. for 1 hour. After adding 24 ml of an SET solution [150 mM NaCl, 1 mM EDTA, and 20 mM Tris-HCl (pH 8.0)], 4 ml of 5% SDS and 400 µl of proteinase K (10 mg/ml) were added to the resulting mixture. Thereafter, the resulting mixture was reacted at 37° C. for 1 hour. After termination of the reaction, phenol-chloroform extraction and subsequent ethanol precipitation were carried out to prepare about 3.2 mg of genomic DNA.

(2) Preparation of Cosmid Protein Library

Four hundred micrograms of the genomic DNA from *Pyrococcus furiousus* DSM3638 was partially digested with Sau3A1 and fractionated by size into 35 to 50 kb fractions by density gradient ultracentrifugation method. One microgram of the triple helix cosmid vector (manufactured by Stratagene) was digested with XbaI, dephosphorylated using an alkaline phosphatase (manufactured by Takara Shuzo Co., Ltd.), and further digested with BamHI. The resulting treated vector was subjected to ligation after mixing with 140 µg of the above 35 to 50 kb DNA fractions. The genomic DNA fragment from *Pyrococcus furiousus* was packaged into lambda phage particles by in vitro packaging method using "GIGAPACK GOLD" (manufactured by Stratagene), to prepare a library. A portion of the obtained library was then transduced into *E. coli* DH5αMCR. Several transformants out of the resulting transformants were selected to prepare a cosmid DNA. After confirmation of the presence of an insert of appropriate size, about 500 transformants were again selected from the above library, and each was separately cultured in 150 ml of an LB medium (10 g/l trypton, 5 g/l yeast extract, 5 g/l NaCl, pH 7.2) containing 100 µg/ml ampicillin. The resulting culture was centrifuged, and the harvested cells were suspended in 1 ml of 20 mM Tris-HCl at a pH of 8.0, and the resulting suspension was then heat-treated at 100° C. for 10 minutes. Next, ultrasonication was carried out, and a heat treatment was carried out again at 100° C. for 10 minutes. The lysate obtained as a supernatant after centrifugation was used as a cosmid protein library.

(3) Assay of DNA Polymerase Activity

The DNA polymerase activity was assayed using calf thymus DNA (manufactured by Worthington) activated by DNase I treatment (activated DNA) as a substrate. DNA activation and assay of DNA polymerase activity were carried out by the method described in *DNA Polymerase from Escherichia coli*, 263–276 (authored by C. C. Richardson), published by Harper & Row, edited by D. R. Davis.

An assay of enzyme activity was carried out by the following method. Specifically, 50 µl of a reaction solution [20 mM Tris-HCl (pH 7.7), 15 mM $MgCl_2$, 2 mM 2-mercaptoethanol, 0.2 mg/ml activated DNA, 40 µM each of dATP, dCTP, dGTP and dTTP, 60 nM [$^3$H]-dTTP (manufactured by Amersham)], containing a sample for assaying its activity, was prepared and reacted at 75° C. for 15 minutes. A 40 µl portion of this reaction mixture was then spotted onto a DE paper (manufactured by Whatman) and washed with 5% $Na_2HPO_4$ five times. The remaining radioactivity on the DE paper was assayed using a liquid scintillation counter. The amount of enzyme which incorporated 10 nmol of [$^3$H]-dTMP per 30 minutes into the substrate DNA, assayed by the above-described enzyme activity assay method, was defined as one unit of the enzyme.

(4) Selection of Cosmid Clones Containing DNA Polymerase Gene

A reaction mixture comprising 20 mM Tris-HCl (pH 7.7), 2 mM $MgCl_2$, 2 mM 2-mercaptoethanol, 0.2 mg/ml activated DNA, 40 µM each of dATP, dCTP, dGTP and dTTP, 60 nM [$^3$H]-dTTP (manufactured by Amersham) was prepared. One µl of 5 clones each of the respective extracts from the cosmid protein library, namely 5 µl of extracts as for one reaction, was added to 45 µl of this mixture. After the mixture was reacted at 75° C. for 15 minutes, a 40 µl portion of each reaction mixture was spotted onto a DE paper and washed with 5% $Na_2HPO_4$ five times. The remaining radioactivity on the DE paper was assayed using a liquid scintillation counter. A group found to have some activities by primary assay, wherein one group consisted of 5 clones, was separated into one clone each from the 5 clones, and then secondary assay was carried out for each clone. Since it had been already known that the cosmid DNA library included clones containing a known DNA polymerase gene by a hybridization test with the gene as a probe, designated as Clone Nos. 57, 154, 162, and 363, 5 clones possessing DNA synthesis activity other than those clones were found as Clone Nos. 41, 153, 264, 462, and 491.

(5) Preparation of Restriction Endonuclease Map

Cosmids were isolated from the above 5 clones, and each cosmid was digested with BamHI. When examining the resulting migration patterns, there were demonstrated several mutually common bands, predicting that those 5 clones recombine regions with overlaps and slight shifts. With this finding in mind, the DNA inserts in Clone Nos. 264 and 491 were treated to prepare the restriction endonuclease map. The cosmids prepared from both clones were digested with various restriction endonucleases. As a result of determination for respective cleavage sites of KpnI, NotI, PstI, SmaI, XbaI, and XhoI (all manufactured by Takara Shuzo Co., Ltd.), digested into fragments of appropriate sizes, a map as shown in FIG. 1 was obtained.

(6) Subcloning of DNA Polymerase Gene

On the basis of the restriction endonuclease map as shown in FIG. 1, various DNA fragments of about 10 kbp in length were cut out from the cosmid derived from clone No. 264 or 491. The fragments were then subcloned into the pTV118N or pTV119N vector (manufactured by Takara Shuzo Co., Ltd.). The resulting transformant with each of the recombinant plasmids was then subjected to assaying of the thermostable DNA polymerase activity, to demonstrate that a gene for production of a highly thermostable DNA polymerase was present an XbaI-XbaI fragment of about 10 kbp. A plasmid resulting from recombination of the XbaI-XbaI fragment in the pTV118N vector was then named as plasmid pFU1001, and the *Escherichia coli* JM109 transformed with the plasmid was named as *Escherichia coli* JM109/pFUFU1001.

EXAMPLE 2
Determination of Base Sequence of DNA Fragment Containing Novel DNA Polymerase Gene The above XbaI-XbaI fragment, containing the DNA polymerase gene, was again cut out from the plasmid pFU1001 obtained in Example 1 with XbaI, and blunt-ended using a DNA blunting kit (manufactured by Takara Shuzo Co., Ltd.). The resultant was then ligated to the new pTV118N vector, previously linearized with SmaI, in different orientations to yield plasmids for preparing deletion mutants. The resulting plasmids were named as pFU1002 and pFU1003, respectively. Deletion mutants were sequentially prepared from both ends of the DNA insert using these plasmids. The Kilo-Sequence deletion kit (manufactured by Takara Shuzo Co., Ltd.) applying Henikoff's method (*Gene,* 28, 351–359) was used for the above preparation. The 3'-overhanging type and 5'-overhanging type restriction endonucleases used were PstI and XbaI, respectively. The base sequence of the insert was determined by the dideoxy method using the BcaBEST dideoxy sequencing kit (manufactured by Takara Shuzo Co., Ltd.) with the various deletion mutants as templates.

An 8,450 bp sequence in the base sequence determined is shown by SEQ ID NO:5 in Sequence Listing. As a result of analysis of the base sequence, there were revealed six open reading frames (ORFs) capable of encoding proteins, present at positions corresponding to Base Nos. 123–614 (ORF1), 611–1381 (ORF2), 1384–3222 (ORF3), 3225–7013 (ORF4), 7068–7697 (ORF5), and 7711–8385 (ORF6) in the base sequence as shown by SEQ ID NO:5 in Sequence Listing. The restriction endonuclease map of the about 10 kbp XbaI-XbaI DNA fragment recombined in the plasmid pFU1001 and the location of the above-mentioned ORFs thereon are shown in FIG. 2.

In addition, the thermostable DNA polymerase activity was assayed using the above various deletion mutants. The results demonstrated that the DNA polymerase activity is lost when the deletion involves the ORF3 and ORF4 regions, regardless of whether the deletion started from upstream or downstream. This finding demonstrated that the translation products of the ORF3 and the ORF4 were important in the exhibition of the DNA polymerase activity. The base sequence of the ORF3 is shown by SEQ ID No:1 in Sequence Listing, and the amino acid sequence of the translation product of the ORF3 as deduced from the base sequence is SEQ ID NO:2 in Sequence Listing, respectively. Also, the base sequence of ORF4 is shown by SEQ ID NO:3 in Sequence Listing, and the amino acid sequence of the translation product of ORF4 as deduced from the base sequence is SEQ ID NO:4 in Sequence Listing, respectively.

EXAMPLE 3
Preparation of Purified DNA Polymerase Standard Preparation

The *Escherichia coli* JM109/pFU1001 obtained in Example 1 was cultured in 500 ml of an LB medium (10 g/l trypton, 5 g/l yeast extract, 5 g/l NaCl, pH 7.2) containing ampicillin at a concentration of 100 µg/ml. When the culture broth turbidity reached 0.6 in $A_{600}$, an inducer, isopropyl-β-D-thiogalactoside (IPTG) was added and cultured for 16 hours. After harvesting, the harvested cells were suspended in 37 ml of a sonication buffer [50 mM Tris-HCl, pH 8.0, 0.2 mM 2-mercaptoethanol, 10% glycerol, 2.4 mM PMSF (phenylmethanesulfonyl fluoride)] and applied to an ultrasonic disrupter. Forty-two milliliters of a crude extract was recovered as a supernatant by centrifugation at 12,000 rpm for 10 minutes, which was then heat-treated at 80° C. for 15 minutes. Centrifugation was again carried out at 12,000 rpm for 10 minutes to yield 33 ml of a heat-treated enzyme solution. The above solution was then dialyzed with 800 ml of buffer A [50 mM potassium phosphate, pH 6.5, 2 mM 2-mercaptoethanol, 10% glycerol] as an external dialysis liquid for 2 hours×4. After dialysis, 32 ml of the enzyme solution was applied to a RESOURCE Q column (manufactured by Pharmacia) which was previously equilibrated with buffer A, and subjected to chromatography using an FPLC system (manufactured by Pharmacia). A development of chromatogram was carried out on a linear concentration gradient from 0 to 500 mM NaCl. A fraction having a DNA polymerase activity was eluted at 340 mM NaCl.

Ten milliliters of an enzyme solution obtained by collecting as an active fraction was desalted and concentrated by ultrafiltration, and dissolved in buffer A+150 mM NaCl to yield 3.5 ml of an enzyme solution. The resulting enzyme solution was then applied to a Hi Trap Heparin column (manufactured by Pharmacia), previously equilibrated with the same buffer. A chromatogram was developed on a linear concentration gradient from 150 to 650 mM NaCl using an FPLC system, to yield an active fraction eluted at 400 mM NaCl. Five milliliters of this fraction was concentrated to 120 µl of a solution including 50 mM potassium phosphate, pH 6.5, 2 mM 2-mercaptoethanol, and 75 mM NaCl by repeating desalting and concentration using ultrafiltration. The resulting concentrated solution was then applied to a gel filtration column of Superose 6 (manufactured by Pharmacia), previously equilibrated with the same buffer, and eluted with the same buffer. As a result, a fraction having a DNA polymerase activity was eluted at positions corresponding to retention times of 34.7 minutes and 38.3 minutes. It is suggested from the results of comparison with the elution position of molecular weight markers under the same conditions that these activity peaks have molecular weights of about 385 kDa and about 220 kDa, respectively. These molecular weights corresponded to a complex formed by the translation product of ORF3 and the translation product of ORF4 in a molar ratio of 1:2 and another complex formed by the above translation products in a molar ratio of 1:1, respectively. For the former peak, however, since a possibility that a complex is formed by the two translation products in a 2:2 molar ratio cannot be negated, the molecular weight determination error increases as the molecular weight increases.

EXAMPLE 4
(1) Biochemical Properties of DNA Polymerase

For a DNA polymerase preparation forming a complex of the translation products of ORF3 and ORF4 obtained in Example 3, namely the first DNA polymerase-constituting protein and the second DNA polymerase-constituting protein in a ratio at 1:1, optimum $MgCl_2$ and KCl concentrations were firstly assayed. The DNA polymerase activity was assayed in a reaction system containing 20 mM Tris-HCl, pH 7.7, 2 mM 2-mercaptoethanol, 0.2 mg/ml activated DNA, and 40 µM each of dATP, dGTP, dCTP and dTTP in the presence of 2 mM $MgCl_2$, while the KCl concentration was step by step increased from 0 to 200 mM KCl for each 20 mM increment. As a result, the maximum activity was exhibited at a KCl concentration of 60 mM. Next, the DNA polymerase activity was assayed in the same reaction system but in the presence of 60 mM KCl in this time, while the $MgCl_2$ concentration was step by step increased from 0.5 to 25 mM $MgCl_2$ for each 2.5 mM increment, to compare at each concentration. In this case, the maximum activity was exhibited at an $MgCl_2$ concentration of 10 mM, and alternatively, in the absence of KCl the maximum activity was exhibited at an $MgCl_2$ concentration of 17.5 mM.

The optimum pH was then assayed. The DNA polymerase activity was assayed at 75° C. by using potassium phosphate buffers at various pH levels, and preparing a reaction mixture comprising 20 mM potassium phosphate, 15 mM $MgCl_2$, 2 mM 2-mercaptoethanol, 0.2 mg/ml activated DNA, 40 μM each of dATP, dCTP, dGTP and dTTP, and 60 nM [$^3$H]-dTTP. The results are shown in FIG. 3, wherein the abscissa indicates the pH, and the ordinate indicates the radioactivity incorporated in high-molecular DNA. As shown in the figure, the DNA polymerase of the present invention exhibited the maximum activity at a pH of 6.5 to 7.0. When Tris-HCl was used in place of potassium phosphate, the activity increased with alkalinity, and the maximum activity was exhibited at a pH of 8.02, the highest pH level used in the assay.

The heat stability of the DNA polymerase of the present invention was assayed as follows: The purified DNA polymerase was prepared to yield a mixture containing 20 mM Tris-HCl (pH 7.7), 2 mM 2-mercaptoethanol, 10% glycerol, and 0.1% bovine serum albumin, and the resulting mixture was incubated at various temperatures for 30 minutes. The remaining DNA polymerase activity was assayed. The results are shown in FIG. 4, wherein the abscissa indicates the incubation temperature, and the ordinate indicates the remaining activity. As shown in the figure, the present enzyme retained not less than 80% remaining activity even after heat treatment at 80° C. for 30 minutes.

In order to compare the modes of inhibition by inhibitors, the modes of inhibition of the DNA polymerase of the present invention and an α-type DNA polymerase derived from *Pyrococcus furiousus* (Pfu DNA polymerase, manufactured by Stratagene), a known DNA polymerase, were compared using a specific inhibitor of α-type DNA polymerases, aphidicolin. The activity changes were examined, while the aphidicolin concentration was increased from 0 to 2.0 mM in the presence of 20 mM Tris-HCl, pH 7.7, 15 mM $MgCl_2$, 2 mM 2-mercaptoethanol, 0.2 mg/ml activated DNA, and 40 μM each of dATP, dGTP, dCTP and dTTP. As a result, the activity of the Pfu DNA polymerase was decreased to 20% of the original activity at 1.0 mM, while the novel DNA polymerase of the present invention was not inhibited at all even at 2.0 mM.

(2) Primer Extension Reaction

Next, in order to compare the selectivity of the DNA polymerase of the present invention for different forms of substrate DNA, the following template-primer was examined. Aside from the activated DNA used for conventional assay of the activity, those prepared as substrates include a thermal-denatured DNA prepared by treating the activated DNA at 85° C. for 5 minutes; M13-HT Primer prepared by annealing a 45-base synthetic deoxyribooligonucleotide of the sequence as shown by SEQ ID NO:6 in Sequence Listing as a primer to the M13 phage single stranded DNA (M13mp18 ssDNA, manufactured by Takara Shuzo Co., Ltd.); M13-RNA Primer prepared by annealing a 17-base synthetic ribooligonucleotide of the sequence as shown by SEQ ID NO:7 in Sequence Listing as a primer to the same M13 phage single stranded DNA; Poly dA-Oligo dT prepared by mixing polydeoxyadenosine (Poly dA, manufactured by Pharmacia) and oligodeoxythymidine (Oligo dT, manufactured by Pharmacia) in a 20:1 molar ratio; and Poly A-Oligo dT prepared by mixing polyadenosine (Poly A, manufactured by Pharmacia) and oligodeoxythymidine in a 20:1 molar ratio.

The DNA polymerase activity was assayed using these substrates in place of the activated DNA. The relative activity of each substrate when the activity obtained in the case of using an activated DNA as a substrate is defined as 100 is shown in Table 1. For comparison, the Pfu DNA polymerase and the Taq DNA polymerase derived from *Thermus aquaticus* (TaKaRa Taq, manufactured by Takara Shuzo Co., Ltd.) were also examined in the same manner. As shown in Table 1, in comparison with other DNA polymerases, the novel DNA polymerase of the present invention exhibited higher activity when the substrate used was the M13-HT Primer rather than the activated DNA, demonstrating that the novel DNA polymerase of the present invention is especially suitable for primer extension reaction.

The primer extension activity was further investigated extensively. The M13-HT Primer, previously labeled with [γ-$^{32}$P]-ATP (manufactured by Amersham) and T4 polynucleotide kinase (manufactured by Takara Shuzo Co., Ltd.) at the 5'-end, was used as a substrate. Ten microliters of a reaction mixture [20 mM Tris-HCl (pH 7.7), 15 mM $MgCl_2$, 2 mM 2-mercaptoethanol, 270 μM each of dATP, dGTP, dCTP and dTTP] containing the above substrate in a final concentration of 0.05 μg/pl and various DNA polymerases in amounts providing 0.05 units of activity as assayed with the activated DNA as a substrate was reacted at 75° C. for 1, 2, 3, or 4 minutes. After termination of the reaction, 2 μl of a reaction stop solution (95% formaldehyde, 20 mM EDTA, 0.05% bromophenol blue, 0.05% xylenecyanol) was added, subjected to thermal denaturation treatment at 95° C. for 3 minutes. Two microliters of the reaction mixture was then subjected to electrophoresis using polyacrylamide gel containing 8 M urea and subsequently subjected to a preparation of autoradiogram. Also, in order to examine the extension activity in the presence of the activated DNA as a competitor substrate, the activated DNA was added to the above reaction mixture to a final concentration of 0.4 μg/ml, and subjected to a preparation of an autoradiogram by the same procedures as described above. The autoradiogram obtained is shown in FIG. 6.

In the figure, Pol, Pfu, and Taq show the results for the DNA polymerase of the present invention, the Pfu DNA polymerase and the Taq DNA polymerase, respectively. In addition, 1, 2, 3, and 4 each indicates reaction time (min). In the figure, the representation "−" and "+" show the results obtained in the absence and in the presence, respectively, of the activated DNA. The lanes G, A, T, and C at the left end of the figure also show the results of electrophoresis of the reaction products obtained by a chain termination reaction by the dideoxy method using the same substrate as above, which were used to estimate the length of each extension product. As shown in the figure, the DNA polymerase of the present invention exhibited superior primer extension activity than those of the Pfu DNA polymerase and the Taq DNA polymerase. It was also shown that the DNA polymerase of the present invention was unlikely to be inhibited by the activated DNA, in contrast to the Taq DNA polymerase, which exhibited relatively higher primer extension activity in the absence of the activated DNA, was markedly inhibited by the addition of the activated DNA in great excess. From the above finding, it was confirmed that the DNA polymerase of the present invention possesses high affinity especially to primer extension type substrates having a form in which a single primer was annealed to a single stranded template DNA.

(3) Presence or Absence of Associated Exonuclease Activity

The exonuclease activity of the DNA polymerase of the present invention was assessed as follows: As a substrate for 5'→3' exonuclease activity detection, a DNA fragment labeled with $^{32}$P at the 5'-end was prepared by a process comprising digesting a pUC119 vector (manufactured by Takara Shuzo Co., Ltd.) with SspI (manufactured by Takara Shuzo Co., Ltd.), separating the resulting 386 bp DNA fragment by agarose gel electrophoresis, purifying the fragment, and labeling with [γ-$^{32}$P]-ATP and polynucleotide kinase. Also, as a substrate for 3'→5' exonuclease activity detection, a DNA fragment labeled with $^{32}$P at 3'-end was prepared by a process comprising digesting a pUC119 vector with Sau3AI, separating the resulting 341 bp DNA fragment by agarose gel electrophoresis, purifying the fragment, and carrying out a fill-in reaction using [γ-$^{32}$P]-CTP (manufactured by Amersham) and the Klenow fragment (manufactured by Takara Shuzo Co., Ltd.). The labeled DNAs were purified by gel filtration with NICK COLUMN (manufactured by Pharmacia) and used in the subsequent reaction. To a reaction solution [20 mM Tris-HCl (pH 7.7), 15 mM $MgCl_2$, 2 mM 2-mercaptoethanol] containing 1 ng of these labeled DNAS, 0.015 units of DNA polymerase was added, and the resulting mixture was reacted at 75° C. for 2.5, 5, and 7.5 minutes. The DNAs were precipitated by adding ethanol. The radioactivity existing in the supernatant was assayed using a liquid scintillation counter, and the amount of degradation by the exonuclease activity was calculated. The DNA polymerase of the present invention was shown to possess potent 3'→5' exonuclease activity, while no 5'→3'exonuclease activity was observed. The 3'→5' exonuclease activity of the Pfu DNA polymerase, known to possess potent 3'→5' exonuclease activity, was also assayed in the same manner as above. The results are together shown in FIG. 5.

In the figure, the abscissa indicates the reaction time, and the ordinate indicates the ratio of radioactivity released into the supernatant relative to the radioactivity contained in the entire reaction mixture. Also, the open circles indicate the results for the DNA polymerase of the present invention, and the solid circles indicate those for the Pfu DNA polymerase. As shown in the figure, the DNA polymerase of the present invention showed potent 3'→5' exonuclease activity of the same level as that of the Pfu DNA polymerase, known to possess high accuracy of DNA synthesis owing to high 3'→5' exonuclease activity.

(4) Comparison of Accuracy of DNA Synthesis Reaction

The accuracy of DNA synthesis reaction by DNA polymerases was examined using a pUC118 vector (manufactured by Takara Shuzo Co., Ltd.), partially made single stranded (gapped duplex plasmid, as a template. The single stranded pUC118 vector was prepared by the method described in *Molecular Cloning: A Laboratory Manual,* 2nd ed., 4.44–4.48, published by Cold Spring Harbor Laboratory in 1989, edited by T. Maniatis et al., using a helper phage M13KO7 (manufactured by Takara Shuzo Co., Ltd.) with *Escherichia coli* MV1184 (manufactured by Takara Shuzo Co., Ltd.) as a host. The double stranded DNA was prepared by digesting the pUC118 vector with PvuII (manufactured by Takara Shuzo Co., Ltd.), subjecting the digested vector to agarose gel electrophoresis, and recovering a DNA fragment of about 2.8 kbp.

One microgram of the above single stranded DNA and 2 μg of the double stranded DNA were mixed to make 180 μl of a mixture with sterile distilled water, and the solution was then incubated at 70° C. for 10 minutes. Thereafter, twenty microliters of 20×SSC was added to the resulting mixture, and the mixture was further kept standing at 60° C. for 10 minutes. The DNA was recovered by subjecting to ethanol precipitation. A portion thereof was subjected to agarose gel electrophoresis, and it was confirmed that a gapped duplex plasmid was obtained. Thirty microliters of a reaction mixture [10 mM Tris-HCl, pH 8.5, 50 mM KCl, 10 mM $Mgcl_2$, 1 mM each of dATP, dCTP, dGTP and dTTP], containing an amount one-tenth that of the resulting gapped duplex plasmid was incubated at 700° C. for 3 minutes, after which 0.5 units of DNA polymerase was added thereto, and a DNA synthesis reaction was carried out at 70° C. for 10 minutes. After termination of the reaction, *Escherichia coli* DH5α (manufactured by BRL) was transformed using 10 μl of the reaction mixture. The resulting transformant was cultured at 37° C. for 18 hours on an LB plate containing 100 μg/ml ampicillin, 0.1 mM IPTG, and 40 μg/ml 5-bromo-4-chloro-3-indolyl-β-D-galactoside. The white or blue colonies formed on the plate were counted, and the formation rate of white colonies which were resulted from a DNA synthesis error was calculated. As a result, the white colony formation rate (%) was 3.18% when the Tag DNA polymerase was used as the DNA polymerase, in contrast to a lower formation rate of 1.61% when the DNA polymerase of the present invention was used.

(5) Application to PCR

In order to compare the performance of the DNA polymerase of the present invention in PCR with that of the Taq DNA polymerase, PCR was carried out with λ-DNA as a template. The reaction mixture for the DNA polymerase of the present invention had the following composition: 10 mM Tris-HCl (pH 9.2), 3.5 mM $MgCl_2$, 75 mM KCl, 400 μM each of dATP, dCTP, dGTP and dTTP, 0.01% bovine serum albumin (BSA), and 0.1% Triton X-100. The reaction solution for the Taq DNA polymerase had the following composition: 10 mM Tris-HCl (pH 8.3), 1.5 mM $MgCl_2$, 50 mM KCl, and 400 μM each of dATP, dCTP, dGTP and dTTP. Fifty microliters of a reaction mixture containing 5.0 ng/50 μl λ-DNA (manufactured by Takara Shuzo Co., Ltd.), 10 pmol/50 μl each of primer λ1 and primer λ11, and 3.7 units/50 μl DNA polymerase was prepared. The base sequences of the primer λ1 and the primer λ11 are shown by SEQ ID NO:8 and SEQ ID NO:9 in Sequence Listing, respectively. After, a 30-cycle PCR was carried out with the above reaction mixture, wherein one cycle is defined at 98° C. for 10 seconds and at 68° C. for 10 seconds. Five microliters of the reaction mixture was subjected to agarose gel electrophoresis, and the amplified DNA fragment was confirmed by staining with ethidium bromide. As a result, it was demonstrated that the DNA fragment amplification was not found when the Taq DNA polymerase was used, in contrast to the DNA polymerase of the present invention where amplification of a DNA fragment of about 20 kbp was confirmed.

The experiment was then carried out by changing the primer to the primer λ1 and the primer λ10. The base sequence of the primer λ10 is shown by SEQ ID NO:10 in Sequence Listing. Twenty-five microliters of a reaction mixture having a similar composition to that shown above and containing 2.5 ng of λ-DNA, 10 pmol of the primer λ1 and the primer λ10, respectively, and 3.7 units of DNA polymerase was prepared. The reaction mixture was reacted in 5 cycles under the same reaction conditions as those described above, and 5 μl of the reaction mixture was subjected to agarose gel electrophoresis and stained with ethidium bromide. It was demonstrated that no specific amplification was observed when the Taq DNA polymerase was used, in contrast to the DNA polymerase of the present invention where a DNA fragment of about 15 kbp was amplified.

EXAMPLE 5

(1) Construction of Plasmid for Expression of ORF3 Translation Product Alone

PCR was carried out using a mutant plasmid 6-82 as a template, the mutant plasmid being prepared by deleting the portion immediately downstream of the ORF3 from the DNA insert in the plasmid pFU1002 described in Example 2, wherein the ORF1 to the ORF6 were located downstream of the lac promoter on the vector and also using a primer M4 (manufactured by Takara Shuzo Co., Ltd) and the primer NO:3 whose base sequence is shown by SEQ ID:11 in Sequence Listing. The DNA polymerase used for the PCR was the Pfu DNA polymerase (manufactured by Stratagene), which possessed high accuracy of synthesis reaction. A 25-cycle reaction of 100 μl of a reaction mixture for PCR [20 mM Tris-HCl, pH 8.2, 10 mM KCl, 20 mM $MgCl_2$, 6 mM $(NH_4)_2SO_4$, 0.2 mM each of dATP, dCTP, dGTP and dTTP, 1% Triton X-100, 0.01% BSA] containing 1 ng of a template DNA, 25 pmol of each primer, and 2.5 units of the Pfu DNA polymerase was carried out, wherein one cycle is defined as at 94° C. for 0.5 minutes, at 55° C. for 0.5 minutes and at 72° C. for 2 minutes. The amplified DNA fragment of about 2 kbp was digested with NcoI and SphI (each manufactured by Takara Shuzo Co., Ltd.) and inserted into between the NcoI-SphI sites of the pTV118N vector (manufactured by Takara Shuzo Co., Ltd.) to prepare a plasmid pFU-ORF3. The DNA insert in the above plasmid contains ORF3 alone in translatable conditions.

(2) Construction of Plasmid for Expression of ORF4 Translation Product Alone

PCR was carried out using a mutant plasmid 6-2 as a template, the mutant plasmid being prepared by deleting the portion downstream of the center portion of the ORF4 from the DNA insert in the above-described plasmid pFU1002, the primer M4, and the primer NO4 of which the base sequence is shown by SEQ ID NO:12 in Sequence Listing. The reaction was carried out under the same conditions as those for Example 5-(1) described above, except that the template DNA was replaced with the plasmid 6-2, and the primer NO3 was replaced with the primer NO:04. A DNA fragment of about 1.6 kbp obtained by digesting the above amplified DNA fragment with NcoI and NheI (manufactured by Takara Shuzo Co., Ltd.), together with an about 3.3 kbp NheI-SaI fragment, including the latter portion of ORF4, isolated from the above plasmid pFU1002 was inserted between the NcoI-XhoI sites of a pET15b vector (manufactured by Novagen) to prepare a plasmid pFU-ORF4. The DNA insert in the plasmid contains ORF4 alone in translatable conditions.

(3) Reconstitution of DNA Polymerase with ORF3 and ORF4 Translation Products

The *Escherichia coli* JM109 transformed with the above-described plasmid pFU-ORF3, *Escherichia coli* JM109/pFU-ORF3, and the *Escherichia coli* HMS174 transformed with the above-described plasmid pFU-ORF4, *Escherichia coli* HMS174/pFU-ORF4, were separately cultured, and then the translation products of the two ORFs expressed in their cells were purified. The cultivation of the transformants and the preparation of the crude extracts were carried out by the methods described in Example 3. Purification of both translation products was carried out using columns such as RESOURCE Q, HiTrap Heparin, and Superose 6, while the behaviors of the translation products on SDS-PAGE were monitored. It was confirmed that although neither of the ORF translation products thus purified exhibited the DNA polymerase activity when assayed alone, thermostable DNA polymerase activity was exhibited when they were mixed together.

Industrial Applicability

The present invention can provide a novel DNA polymerase possessing both high primer extensibility and high 3'→5' exonuclease activity. The enzyme is suitable for its use for PCR method, which is useful for a reagent for genetic engineering investigation. It is also possible to produce the enzyme by genetic engineering using the genes encoding the DNA polymerase of the present invention.

What is claimed is:

1. An isolated and purified DNA polymerase, characterized in that said DNA polymerase possesses the following properties:
1) exhibiting higher polymerase activity when assayed by using as a substrate a complex resulting from primer annealing to a single stranded template DNA, compared to using an activated DNA as a substrate;
2) possessing a 3'→5' exonuclease activity;
3) amplifying a DNA fragment of about 20 kbp, when polymerase chain reaction (PCR) is carried out using λ-DNA as a template under the following conditions:
PCR conditions:
(a) a composition of reaction mixture: containing 10 mM Tris-HCl (pH 9.2), 3.5 mM MgCl$_2$, 75 mM KCl, 400 µM each of dATP, dCTP, dGTP and dTTP, 0.01% bovine serum albumin, 0.1% Triton X-100, 5.0 ng/50 µl λ-DNA, 10 pmole/50 µl primer λ1 (SEQ ID NO:8), primer λ11 (SEQ ID NO:9), and 3.7 units/50 µl DNA polymerase;
(b) reaction conditions: carrying out a 30-cycle PCR, wherein one cycle is defined as at 98° C. for 10 seconds and at 68° C. for 10 minutes;
wherein said DNA polymerase comprises a first polypeptide and a second polypeptide, which are non-covalently bonded to form a complex,
wherein said first polypeptide comprises:
(I) the amino acid sequence encoded by a DNA of SEQ ID NO:1, or
(II) an amino acid sequence encoded by a DNA, the complement thereof hybridizing to the DNA of SEQ ID NO:1 under stringent conditions; and
wherein said second polypeptide comprises:
(I) the amino acid sequence encoded by a DNA of SEQ ID NO:3, or
(II) an amino acid sequence encoded by a DNA, the complement thereof hybridizing to the DNA of SEQ ID NO:3 under stringent conditions.

2. The isolated and purified DNA polymerase according to claim 1, characterized in that said DNA polymerase exhibits a lower error rate in DNA synthesis as compared to Taq DNA polymerase.

3. The isolated and purified DNA polymerase according to claim 1, wherein the molecular weight as determined by gel filtration method is about 220 kDa or about 385 kDa.

4. An isolated and purified DNA polymerase acccording to claim 1, characterized in that said DNA polymerase exhibits a DNA polymerase activity wherein said DNA polymerase comprises a first polypeptide and a second polypeptide, which are non-covalently bonded to form a complex,
wherein the molecular weight of said first polypeptide is about 90,000 Da and the molecular weight of said second polypeptide is about 140,000 Da as determined by SDS-PAGE, and
wherein said DNA polymerase possesses the following properties:
1) exhibiting higher polymerase activity when assayed by using as a substrate a complex resulting from primer annealing to a single stranded template DNA, compared to using an activated DNA as a substrate;
2) possessing a 3'→5' exonuclease activity;
3) amplifying a DNA fragment of about 20 kbp, when polymerase chain reaction (PCR) is carried out using λ-DNA as a template under the following conditions:
PCR conditions:
(a) a composition of reaction mixture: containing 10 mM Tris-HCl (pH 9.2), 3.5 mM MgCl$_2$, 75 mM KCl, 400 µM each of dATP, dCTP, dGTP and dTTP, 0.01% bovine serum albumin, 0.1% Triton X-100, 5.0 ng/50 µl λ-DNA, 10 pmole/ 50 µl primer λ1 (SEQ ID NO:8), primer λ11 (SEQ ID NO:9), and 3.7 units/50 µl DNA polymerase;
(b) reaction conditions: carrying out a 30-cycle PCR, wherein one cycle is defined as at 98° C. for 10 seconds and at 68° C. for 10 minutes.

5. An isolated and purified first polypeptide comprising the amino acid sequence as shown by SEQ ID NO:2, wherein the first polypeptide exhibits DNA polymerase activity and the following properties:
1) exhibiting higher polymerase activity when assayed by using as a substrate a complex resulting from primer annealing to a single stranded template DNA, compared to using an activated DNA as a substrate;

2) possessing a 3'→5' exonuclease activity;
3) amplifying a DNA fragment of about 20 kbp, when polymerase chain reaction (PCR) is carried out using λ-DNA as a template under the following conditions: PCR conditions:
    (a) a composition of reaction mixture: containing 10 mM Tris-HCl (pH 9.2), 3.5 mM MgCl$_2$, 75 mM KCl, 400 μM each of dATP, dCTP, dGTP and dTTP, 0.01% bovine serum albumin, 0.1% Triton X-100, 5.0 ng/50 μl λ-DNA, 10 pmole/50 μl primer λ1 (SEQ ID NO:8), primer λ11 (SEQ ID NO:9), and 3.7 units/50 μl DNA polymerase;
    (b) reaction conditions: carrying out a 30-cycle PCR, wherein one cycle is defined as at 98° C. for 10 seconds and at 68° C. for 10 minutes,
when combined with a second polypeptide of the amino acid sequence as shown by SEQ ID NO:4.

6. An isolated and purified second polypeptide comprising the amino acid sequence as shown by SEQ ID NO:4, wherein the second polypeptide exhibits DNA polymerase activity and the following properties:
1) exhibiting higher polymerase activity when assayed by using as a substrate a complex resulting from primer annealing to a single stranded template DNA, compared to using an activated DNA as a substrate;
2) possessing a 3'→5' exonuclease activity;
3) amplifying a DNA fragment of about 20 kbp, when polymerase chain reaction (PCR) is carried out using λ-DNA as a template under the following conditions: PCR conditions:
    (a) a composition of reaction mixture: containing 10 mM Tris-HCl (pH 9.2), 3.5 mM MgCl$_2$, 75 mM KCl, 400 μM each of dATP, dCTP, dGTP and dTTP, 0.01% bovine serum albumin, 0.1% Triton X-100, 5.0 ng/50 μl λ-DNA, 10 pmole/50 μl primer λ1 (SEQ ID NO:8), primer λ11 (SEQ ID NO:9), and 3.7 units/50 μl DNA polymerase;
    (b) reaction conditions: carrying out a 30-cycle PCR, wherein one cycle is defined as at 98° C. for 10 seconds and at 68° C. for 10 minutes,
when combined with a first polypeptide of the amino acid sequence as shown by SEQ ID NO:2.

7. An isolated DNA encoding a first polypeptide comprising a base sequence selected from the group consisting of:
(I') a base sequence encoding the amino acid sequence as shown by SEQ ID NO:2,
(II') the base sequence as shown by SEQ ID NO:1, and
(III') a base sequence of a DNA, the complement thereof hybridizing to DNA of SEQ ID NO:1 under stringent conditions,
wherein the first polypeptide encoded by the base sequence exhibits DNA polymerase activity and the following properties:
1) exhibiting higher polymerase activity when assayed by using as a substrate a complex resulting from primer annealing to a single stranded template DNA, compared to using an activated DNA as a substrate;
2) possessing a 3'→5' exonuclease activity;
3) amplifying a DNA fragment of about 20 kbp, when polymerase chain reaction (PCR) is carried out using λ-DNA as a template under the following conditions: PCR conditions:
    (a) a composition of reaction mixture: containing 10 mM Tris-HCl (pH 9.2), 3.5 mM MgCl$_2$, 75 mM KCl, 400 μM each of dATP, dCTP, dGTP and dTTP, 0.01% bovine serum albumin, 0.1% Triton X-100, 5.0 ng/50 μl λ-DNA, 10 pmole/50 μl primer λ1 (SEQ ID NO:8), primer λ11 (SEQ ID NO:9), and 3.7 units/50 μl DNA polymerase;
    (b) reaction conditions: carrying out a 30-cycle PCR, wherein one cycle is defined as at 98° C. for 10 seconds and at 68° C. for 10 minutes,
when combined with a second polypeptide of the amino acid sequence as shown by SEQ ID NO:4.

8. An isolated DNA encoding a second polypeptide comprising a base sequence selected from the group consisting of:
(I') a base sequence encoding the amino acid sequence as shown by SEQ ID NO:4,
(II') the base sequence as shown by SEQ ID NO:3, and
(III') a base sequence of a DNA, the complement thereof hybridizing to DNA of SEQ ID NO:3 under stringent conditions, wherein the second polypeptide encoded by the base sequence exhibits DNA polymerase activity and the following properties:
1) exhibiting higher polymerase activity when assayed by using as a substrate a complex resulting from primer annealing to a single stranded template DNA, compared to using an activated DNA as a substrate;
2) possessing a 3'→5' exonuclease activity;
3) amplifying a DNA fragment of about 20 kbp, when polymerase chain reaction (PCR) is carried out using λ-DNA as a template under the following conditions: PCR conditions:
    (a) a composition of reaction mixture: containing 10 mM Tris-HCl (pH 9.2), 3.5 mM MgCl$_2$, 75 mM KCl, 400 μM each of dATP, dCTP, dGTP and dTTP, 0.01% bovine serum albumin, 0.1% Triton X-100, 5.0 ng/50 μl λ-DNA, 10 pmole/50 μl primer λ1 (SEQ ID NO:8), primer λ11 (SEQ ID NO:9), and 3.7 units/50 μl DNA polymerase;
    (b) reaction conditions: carrying out a 30-cycle PCR, wherein one cycle is defined as at 98° C. for 10 seconds and at 68° C. for 10 minutes,
when combined with a first polypeptide of the amino acid sequence as shown by SEQ ID NO:2.

9. A method for producing a DNA polymerase, comprising the steps of:
culturing a transformant containing both a gene encoding a first polypeptide, which contains DNA encoding the amino acid sequence of SEQ ID NO:2, a DNA of the base sequence of SEQ ID NO:1, or a DNA, the complement thereof which hybridizes to the base sequence of SEQ ID NO:1 under stringent conditions,
and a gene encoding a second polypeptide, which contains DNA encoding the amino acid sequence of SEQ ID NO:4, a DNA of the base sequence of SEQ ID NO:3, or a DNA, the complement thereof which hybridizes to the base sequence of SEQ ID NO:3 under stringent conditions; and
collecting the DNA polymerase from the resulting culture wherein the molecular weight of said first polypeptide is about 90,000 Da and that of said second polypeptide is about 140,000 Da as determined by SDS-PAGE, and wherein said DNA polymerase possesses the following properties:
1) exhibiting higher polymerase activity when assayed by using as a substrate a complex resulting from primer annealing to a single stranded template DNA, compared to using an activated DNA as a substrate;

2) possessing a 3'→5' exonuclease activity;

3) amplifying a DNA fragment of about 20 kbp, when polymerase chain reaction (PCR) is carried out using λ-DNA as a template under the following conditions:

PCR conditions:

(a) a composition of reaction mixture: containing 10 mM Tris-HCl (pH 9.2), 3.5 mM $MgCl_2$, 75 mM KCl, 400 µM each of dATP, dCTP, dGTP and dTTP, 0.01% bovine serum albumin, 0.1% Triton X-100, 5.0 ng/50 µl λ-DNA, 10 pmole/50 µl primer λ1 (SEQ ID NO:8), primer λ11 (SEQ ID NO:9), and 3.7 units/50 µl DNA polymerase;

(b) reaction conditions: carrying out a 30-cycle PCR, wherein one cycle is defined as at 98° C. for 10 seconds and at 68° C. for 10 minutes.

10. A method for producing a DNA polymerase, comprising the steps of:

culturing a transformant containing a gene encoding a first polypeptide, which contains DNA encoding the amino acid sequence of SEQ ID NO:2, a DNA of the base sequence of SEQ ID NO:1, or a DNA, the complement thereof which hybridizes to the base sequence of SEQ ID NO:1 under stringent conditions, and a transformant containing a gene encoding a second polypeptide, which contains DNA encoding the amino acid sequence of SEQ ID NO:4, a DNA of the base sequence of SEQ ID NO:3, or a DNA, the complement thereof which hybridizes to the base sequence of SEQ ID NO:3 under stringent conditions;

combining the first polypeptide contained in the resulting culture and the second polypeptide contained in the resulting culture, thereby allowing non-covalent bonding to form a DNA polymerase as a complex; and collecting the DNA polymerase, wherein the molecular weight of said first polypeptide is about 90,000 Da and the molecular weight of said second polypeptide is about 140,000 Da as determined by SDS-PAGE, and wherein said DNA polymerase possesses the following properties:

1) exhibiting higher polymerase activity when assayed by using as a substrate a complex resulting from primer annealing to a single stranded template DNA, compared to using an activated DNA as a substrate;

2) possessing a 3'→5' exonuclease activity;

3) amplifying a DNA fragment of about 20 kbp, when polymerase chain reaction (PCR) is carried out using λ-DNA as a template under the following conditions:

PCR conditions:

(a) a composition of reaction mixture: containing 10 mM Tris-HCl (pH 9.2), 3.5 mM $MgCl_2$, 75 mM KCl, 400 µM each of dATP, dCTP, dGTP and dTTP, 0.01% bovine serum albumin, 0.1% Triton X-100, 5.0 ng/50 µl λ-DNA, 10 pmole/50 µl primer λ1 (SEQ ID NO:8), primer λ11 (SEQ ID NO:9), and 3.7 units/50 µl DNA polymerase;

(b) reaction conditions: carrying out a 30-cycle PCR, wherein one cycle is defined as at 98° C. for 10 seconds and at 68° C. for 10 minutes.

11. A recombinant first polypeptide encoded by the isolated DNA of claim 7, wherein the first polypeptide exhibits DNA polymerase activity and the following properties:

1) exhibiting higher polymerase activity when assayed by using as a substrate a complex resulting from primer annealing to a single stranded template DNA, compared to using an activated DNA as a substrate;

2) possessing a 3'→5' exonuclease activity;

3) amplifying a DNA fragment of about 20 kbp, when polymerase chain reaction (PCR) is carried out using λ-DNA as a template under the following conditions:

PCR conditions:

(a) a composition of reaction mixture: containing 10 mM Tris-HCl (pH 9.2), 3.5 mM $MgCl_2$, 75 mM KCl, 400 µM each of dATP, dCTP, dGTP and dTTP, 0.01% bovine serum albumin, 0.1% Triton X-100, 5.0 ng/50 µl λ-DNA, 10 pmole/50 µl primer λ1 (SEQ ID NO:8), primer λ11 (SEQ ID NO:9), and 3.7 units/50 µl DNA polymerase;

(b) reaction conditions: carrying out a 30-cycle PCR, wherein one cycle is defined as at 98° C. for 10 seconds and at 68° C. for 10 minutes, when combined with a second polypeptide of the amino acid sequence as shown by SEQ ID NO:4.

12. A recombinant second polypeptide encoded by the isolated DNA of claim 8, wherein the second polypeptide exhibits DNA polymerase activity and the following properties:

1) exhibiting higher polymerase activity when assayed by using as a substrate a complex resulting from primer annealing to a single stranded template DNA, compared to using an activated DNA as a substrate;

2) possessing a 3'→5' exonuclease activity;

3) amplifying a DNA fragment of about 20 kbp, when polymerase chain reaction (PCR) is carried out using λ-DNA as a template under the following conditions:

PCR conditions:

(a) a composition of reaction mixture: containing 10 mM Tris-HCl (pH 9.2), 3.5 mM $MgCl_2$, 75 mM KCl, 400 µM each of dATP, dCTP, dGTP and dTTP, 0.01% bovine serum albumin, 0.1% Triton X-100, 5.0 ng/50 µl λ-DNA, 10 pmole/50 µl primer λ1 (SEQ ID NO:8), primer λ11 (SEQ ID NO:9), and 3.7 units/50 µl DNA polymerase;

(b) reaction conditions: carrying out a 30-cycle PCR, wherein one cycle is defined as at 98° C. for 10 seconds and at 68° C. for 10 minutes, when combined with a first polypeptide of the amino acid sequence as shown by SEQ ID NO:2.

* * * * *